United States Patent [19]

Uhr et al.

[11] Patent Number: 5,378,724
[45] Date of Patent: Jan. 3, 1995

[54] PESTICIDAL SUBSTITUTED 2-ARYLPYRROLES

[75] Inventors: Hermann Uhr; Albrecht Marhold, both of Leverkusen; Stefan Böhm, Köln; Christoph Erdelen, Leichlingen; Ulrike Wachendorff-Neumann, Monheim; Wilhelm Stendel, Wuppertal, all of Germany

[73] Assignee: Bayer Aktiengesellschaft, Leverkusen, Germany

[21] Appl. No.: 131,251

[22] Filed: Oct. 1, 1993

[30] Foreign Application Priority Data

Oct. 8, 1992 [DE] Germany ............... 4233885

[51] Int. Cl.⁶ ............... C07D 207/36; C07D 403/02; A01N 43/36
[52] U.S. Cl. ............... 514/424; 514/422; 548/543; 548/550; 548/551
[58] Field of Search ............... 504/283; 548/543, 550, 548/551, 517; 546/208; 549/596; 514/422, 424

[56] References Cited

U.S. PATENT DOCUMENTS 5,204,341 4/1993 Toja et al. ............... 548/541

FOREIGN PATENT DOCUMENTS

| 347488 | 8/1988 | European Pat. Off. . |
| 434940 | 11/1990 | European Pat. Off. . |
| 484614 | 3/1991 | European Pat. Off. . |
| 481182 | 8/1991 | European Pat. Off. . |
| 549866 | 11/1992 | European Pat. Off. . |
| 0549866 | 7/1993 | European Pat. Off. . |

*Primary Examiner*—David B. Springer
*Attorney, Agent, or Firm*—Sprung Horn Kramer & Woods

[57] ABSTRACT

Pesticidal substituted 2-arylpyrroles of the formula

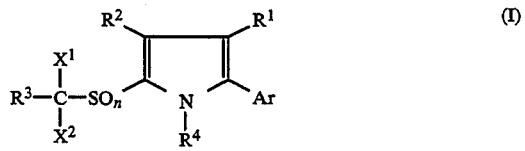

(I)

in which
n represents 0, 1 or 2,
Ar represents optionally substituted aryl,
$R^1$ and $R^2$ independently of one another represent hydrogen or halogen, but at least one of the two radicals $R^1$ or $R^2$ represents halogen,
$R^3$ represents hydrogen, halogen or optionally substituted alkyl,
$X^1$ and $X^2$ independently represent hydrogen or halogen and
$R^4$ represents hydrogen or

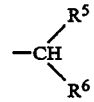

($R^5$ and $R^6$ having various meanings).
The compounds of the formulas

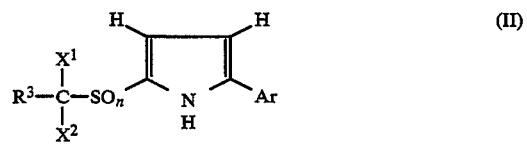

(II)

and

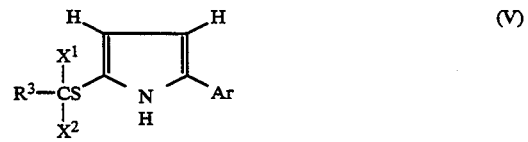

(V)

are also new.

6 Claims, No Drawings

PESTICIDAL SUBSTITUTED 2-ARYLPYRROLES

The present invention relates to new substituted 2-arylpyrroles, to processes and new intermediates for their preparation, and to their use for combating animal pests, in particular insects, arachnids and nematodes which are encountered in agriculture, in forests, in the protection of stored products and materials and in the field of hygiene.

It has already been disclosed that structurally similar cyanopyrroles have a molluscicidal, fungicidal and insecticidal action (see, in this context, EP-A 0,347,488, EP-A 0,358,047, EP-A 0,312,-723, DE-A 4,117,752, EP-A 0,481,182, EP-A 0,484,614). However, the activity and range of action of these compounds is not always entirely satisfactory, in particular when low application rates and concentrations are used.

New substituted 2-arylpyrroles of the general formula (I) have now been found,

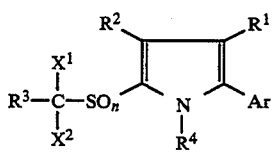

in which
$R^1$ and $R^2$ independently of one another represent hydrogen or halogen, but at least one of the two radicals $R^1$ or $R^2$ represents halogen,
$R^3$ represents hydrogen, halogen or optionally substituted alkyl,
$R^4$ represents hydrogen or

in which $R^5$ represents hydrogen or optionally substituted alkyl and $R^6$ represents hydrogen, optionally substituted alkyl or one of the radicals

or $-O-R^7$,
in which $R^7$ and $R^8$ independently of one another represent hydrogen, alkyl, alkenyl, alkinyl, alkoxycarbonyl, alkenoxycarbonyl, alkinoxycarbonyl or acyl, it also being possible for $R^7$ and $R^8$ together with the N atom to which they are bonded to form a ring,
Ar represents optionally substituted aryl,
$X^1$ and $X^2$ independently of one another represent hydrogen or halogen, and
n represents 0, 1 or 2.

Furthermore, it has been found that—depending on the substituents in each case—the substituted 2-arylpyrroles (I) can be prepared by a range of routes, it being possible for certain sub-groups of end products of the formula (I) simultaneously to be intermediates for the preparation of other end products (I); a survey is given by Diagram 1 below:

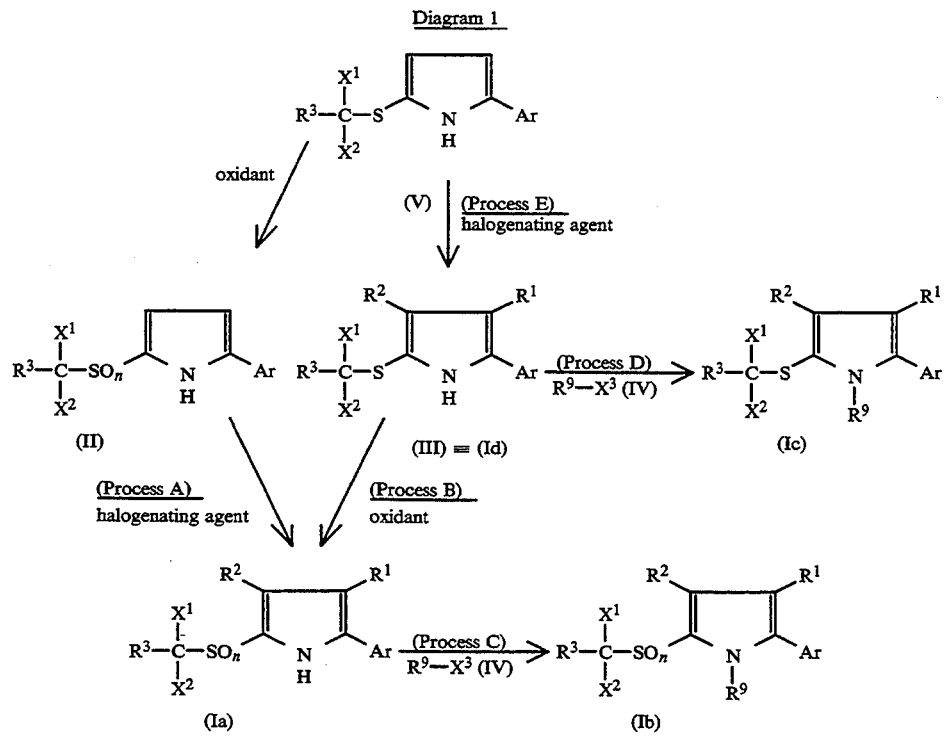

Diagram 1

For example, the substituted 2-arylpyrroles of the general formula (Ia)

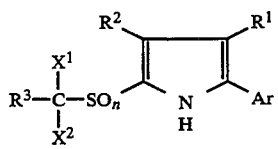
(Ia)

in which $R^1$, $R^2$, $R^3$, $X^1$, $X^2$ and Ar have the above-mentioned meaning and n is 1 or 2, are obtained
when either
A) 2-arylpyrroles of the formula (II)

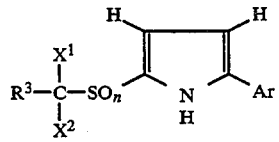
(II)

in which $R^3$, $X^1$, $X^2$ and Ar have the above-mentioned meanings and n is 1 or 2, are reacted with halogenating agents (Process A) or B) 2-arylpyrroles of the formula (III)

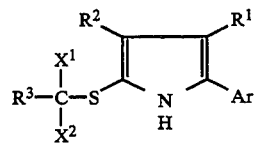
(III)

in which $R^1$, $R^2$, $R^3$, $X^1$, $X^2$ and Ar have the abovementioned meanings, are reacted with oxidants (Process B).

C) 2-Arylpyrroles of the formula (Ib)

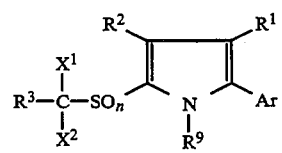
(Ib)

in which $R^1$, $R^2$, $R^3$, $X^1$, $X^2$ and Ar have the abovementioned meaning and n is 1 or 2 and
$R^9$ represents

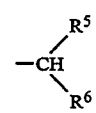

in which $R^5$ and $R^6$ have the abovementioned meaning, are obtained when 2-arylpyrroles of the general formula (Ia) in which $R^1$, $R^2$, $R^3$, $X^1$, $X^2$ and Ar have the abovementioned meaning and 1 or 2, are reacted with compounds of the formula (IV)

$$R^9-X^3 \quad (IV)$$

in which
$R^9$ has the abovementioned meaning and
$X^3$ represents an anionic leaving group,
if appropriate in the presence of bases and/or if appropriate in the presence of diluents (Process C).

D) 2-Arylpyrroles of the formula (Ic)

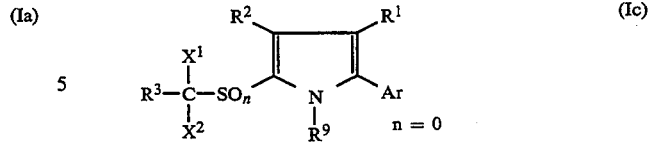
(Ic)

in which $R^1$, $R^2$, $R^3$, $X^1$, $X^2$ and Ar have the abovementioned meaning and
$R^9$ represents

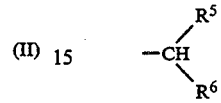

where $R^5$ and $R^6$ have the abovementioned meaning and n is 0,
are furthermore obtained when 2-arylpyrroles of the general formula (III) in which $R^1$, $R^2$, $R^3$, $X^1$, $X^2$ and Ar have the abovementioned meaning are reacted with compounds of the formula (IV)

$$R^9-X^3 \quad (IV)$$

in which
$R^9$ has the abovementioned meaning and
$X^3$ represents an anionic leaving group,
if appropriate in the presence of bases and/or if appropriate in the presence of diluents (Process D).

E) The substituted 2-arylpyrroles of the general formula (Id)

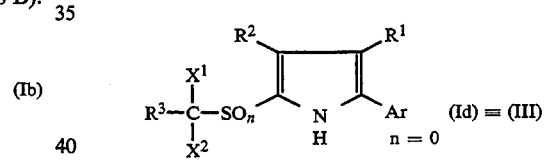
(Id) = (III)

in which $R^1$, $R^2$, $R^3$, $X^1$, $X^2$ and Ar have the abovementioned meaning and n is 0,
are furthermore obtained when 2-arylpyrroles of the formula (V)

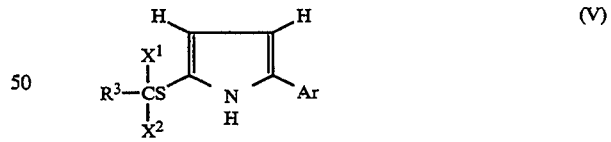
(V)

in which $R^3$, $X^1$, $X^2$ and Ar have the abovementioned meaning are reacted with halogenating agents (Process E).

(The substituted 2-arylpyrroles of the general formula (Id) are identical to the precursors described by the general formula (III)).

Finally, it has been found that the novel substituted 2-arylpyrroles of the formula (I) have highly pronounced biological properties and are suitable especially for combating animal pests, in particular insects, arachnids and nematodes, which are encountered in agriculture, in forests, in the protection of stored products and materials and in the field of hygiene. The novel substituted 2-arylpyrroles of the formula (I) are furthermore suitable for combating phytopathogenic fungi.

Preferred substituted 2-arylpyrroles of the above formula (I) are those in which $R^1$ and $R^2$ independently of one another represent hydrogen, bromine or chlorine, at least one of the radicals $R^1$ or $R^2$ representing bromine or chlorine, $R^3$ represents hydrogen, fluorine, chlorine, bromine or $C_1$-$C_5$-alkyl (which is optionally substituted by identical or different substituents from the series comprising 1 to 5 fluorine, chlorine or bromine atoms), $R^4$ represents hydrogen or

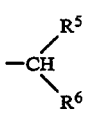

in which $R^5$ represents hydrogen or $C_1$-$C_5$-alkyl (which is optionally substituted by 1 to 5 identical or different halogen atoms, by $C_1$-$C_5$-alkoxy, $C_1$-$C_5$-alkylthio, $C_1$-$C_5$-acyloxy, $C_2$-$C_6$-alkoxycarbonyl, phenyl, cyano or nitro) and $R^6$ represents hydrogen or $C_1$-$C_6$-alkyl (which is optionally substituted by 1 to 5 identical or different halogen atoms, by $C_1$-$C_8$-alkoxy, $C_1$-$C_8$-alkylthio, $C_1$-$C_6$-acyloxy, $C_2$-$C_8$-alkoxycarbonyl, phenyl, cyano or nitro) or in which $R^6$ represents

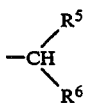

or —O—$R^7$ $R^7$ and $R^8$ independently of one another representing hydrogen, $C_1$-$C_8$-alkyl, $C_3$-$C_8$-alkenyl or $C_3$-$C_8$-alkinyl (the alkyl, alkenyl and alkinyl radicals in each case being optionally substituted by 1 to 6 identical or different halogen atoms, $C_1$-$C_6$-alkoxy, $C_1$-$C_6$-alkylthio, $C_1$-$C_6$-acyloxy, ($C_1$-$C_6$-alkoxy)-carbonyl, optionally substituted phenyl, cyano or nitro), or represent ($C_1$-$C_8$-alkoxy)-carbonyl, ($C_3$-$C_8$-alkenoxy)-carbonyl or ($C_3$-$C_8$-alkinoxy)-carbonyl, (the alkoxy, alkenoxy and alkinoxy radicals in each case being optionally substituted by 1 to 6 identical or different halogen atoms, $C_1$-$C_6$-alkoxy, $C_1$-$C_6$-alkylthio, $C_1$-$C_6$-acyloxy, ($C_1$-$C_6$-alkoxy)-carbonyl, optionally substituted phenyl, cyano or nitro), or represent $C_1$-$C_8$-acyl (which is optionally substituted by 1 to 6 identical or different halogen atoms, $C_1$-$C_6$-alkoxy, $C_1$-$C_6$-alkylthio, $C_1$-$C_6$-acyloxy, ($C_1$-$C_6$-alkoxy)-carbonyl, optionally substituted phenyl, cyano or nitro), or in which $R^7$ and $R^8$ together with the N atom to which they are bonded form a 4- to 8-membered ring, Ar represents phenyl which is optionally monosubstituted to pentasubstituted by identical or different substituents from the series comprising halogen, $C_1$-$C_8$-alkyl $C_2$-$C_8$-alkenyl or $C_2$-$C_8$-alkinyl (it being possible for the alkyl, alkenyl and alkinyl radicals in each case to be optionally substituted by 1 to 6 halogen atoms, $C_1$-$C_5$-alkoxy, $C_1$-$C_5$-alkylthio or by $C_1$-$C_5$-acyloxy, and it being possible for the alkoxy and alkylthio radicals in each case to be substituted by 1-6 halogen atoms), $C_1$-$C_8$-alkoxy, $C_2$-$C_8$-alkenoxy or $C_2$-$C_8$-alkinoxy (it being possible for the alkoxy, alkenoxy and alkinoxy radicals optionally to be substituted by 1 to 6 halogen atoms), $C_1$-$C_8$-alkylthio, $C_2$-$C_8$-alkenylthio or $C_2$-$C_8$-alkinylthio (it being possible for the alkylthio, alkenylthio and alkinylthio radicals in each case to be optionally substituted by 1 to 6 halogen atoms), $C_2$-$C_8$-acyloxy (which is optionally substituted by 1 to 6 halogen atoms), amino (which is optionally substituted by 1 to 2 identical or different alkyl radicals or halogenoalkyl radicals having 1 to 8 carbon-atoms and, if appropriate, 1 to 6 halogen atoms), nitro or cyano, and in which $X^1$ and $X^2$ independently of one another represent hydrogen, fluorine, chlorine or bromine and n represents 0, 1 or 2.

Particularly preferred substituted 2-arylpyrroles of the formula (I) are those in which $R^1$ and $R^2$ independently of one another represent hydrogen, bromine or chlorine, at least one of the two radicals $R^1$ or $R^2$ representing bromine or chlorine, $R^3$ represents hydrogen, fluorine, chlorine, bromine or $C_1$-$C_4$-alkyl (which is optionally substituted by identical or different substituents from the series comprising 1 to 5 fluorine, chlorine or bromine atoms), $R^4$ represents hydrogen or

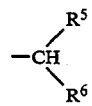

in which $R^5$ represents hydrogen or $C_1$-$C_4$-alkyl (which is optionally substituted by 1 to 5 identical or different halogen atoms, by $C_1$-$C_4$-alkoxy, $C_1$-$C_4$-alkylthio, $C_1$-$C_4$-acyloxy, $C_2$-$C_5$-alkoxycarbonyl, phenyl, cyano or nitro) and $R^6$ represents hydrogen or $C_1$-$C_5$-alkyl (which is optionally substituted by 1 to 5 identical or different halogen atoms, by $C_1$-$C_6$-alkoxy, $C_1$-$C_6$-alkylthio, $C_1$-$C_5$-acyloxy, $C_2$-$C_6$-alkoxycarbonyl, phenyl, cyano or nitro), or in which $R^6$ represents

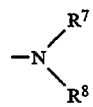

or —O—$R^7$ in which $R^7$ and $R^8$ independently of one another represent hydrogen, $C_1$-$C_6$-alkyl, $C_3$-$C_6$-alkenyl or $C_3$-$C_6$-alkinyl (the alkyl, alkenyl and alkinyl radicals in each case being optionally substituted by 1 to 5 fluorine and/or chlorine atoms, $C_1$-$C_4$-alkoxy, $C_1$-$C_4$-alkylthio, $C_1$-$C_4$-acyloxy, ($C_1$-$C_4$-alkoxy)-carbonyl, optionally substituted phenyl, cyano or nitro), or represent ($C_1$-$C_6$-alkoxy)-carbonyl, ($C_3$-$C_6$-alkenoxy)- or ($C_3$-$C_6$-alkinoxy)-carbonyl (the alkoxy, alkenoxy and alkinoxy radicals in each case optionally being substituted by 1 to 5 fluorine and/or chlorine atoms, $C_1$-$C_4$-alkoxy, $C_1$-$C_4$-alkylthio, $C_1$-$C_4$-acyloxy, ($C_1$-$C_4$-alkoxy)-carbonyl, optionally substituted phenyl, cyano or nitro), or represent $C_1$–$C_6$-acyl (which is optionally substituted by 1 to 5 fluorine and/or chlorine atoms, $C_1$–$C_4$-alkoxy, $C_1$–$C_4$-alkylthio, $C_1$–$C_4$-acyloxy, ($C_1$–$C_4$-alkoxy)-carbonyl, optionally substituted phenyl, cyano or nitro), or $R^7$ and $R^8$ together with the N atom to which they are bonded can be linked via any desired position to form a 4- to 6-membered ring;

in which furthermore

Ar represents phenyl which is optionally monosubstituted to tetrasubstituted by identical or different substituents from the series comprising fluorine, chlorine or bromine, or $C_1$–$C_6$-alkyl, $C_2$–$C_6$-alkenyl or $C_2$–$C_6$-alkinyl (it being possible for the alkyl, alkenyl and alkinyl radicals in each case to be optionally substituted by 1 to 5 fluorine and/or chlorine atoms, $C_1$–$C_4$-alkoxy, $C_1$–$C_4$-alkylthio or by $C_1$–$C_4$-acyloxy, and it being possible for the alkoxy and alkylthio radicals in each case to be substituted by 1 to 5 fluorine and/or chlorine atoms), $C_1$–$C_6$-alkoxy, $C_2$–$C_6$-alkenoxy or $C_2$–$C_6$-alkinoxy (the alkoxy, alkenoxy and alkinoxy radicals optionally being substituted by 1 to 5 fluorine and/or chlorine atoms), $C_1$–$C_6$-alkylthio, $C_2$–$C_6$-alkenylthio or $C_2$–$C_6$-alkinylthio (the alkylthio, alkenylthio and alkinylthio radicals optionally being substituted by 1 to 5 fluorine and/or chlorine atoms), $C_2$–$C_6$-acyloxy (which is optionally substituted by 1 to 5 fluorine and/or chlorine atoms), amino (which is optionally substituted by 1 to 2 identical or different alkyl radicals which have 1 to 6 carbon atoms and which can be substituted by 1 to 5 fluorine and/or chlorine atoms), nitro or cyano, and in which $X^1$ and $X^2$ independently of one another represent hydrogen, fluorine or chlorine and n represents 0, 1 or 2.

The abovementioned general or preferred definitions of radicals or explanations apply to the end products and, analogously, to the starting materials and intermediates. These definitions of radicals can be combined with each other as desired, that is to say combinations between the particular preferred meanings are also possible.

If, according to Preparation Process A, 2-(4-chlorophenyl)-5-(trifluoromethylsulphonyl)-pyrrole and bromine are used as starting materials, the course of the reaction can be represented by the following equation:

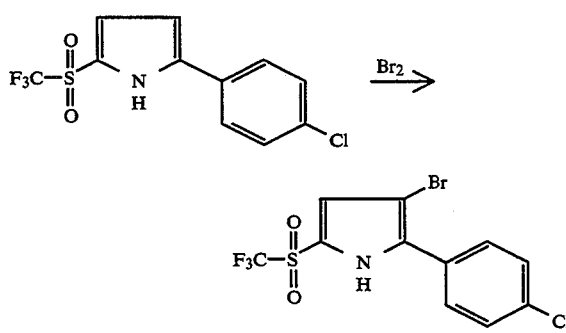

If, according to Process B, 2-(4-chlorophenyl)-3,4-dibromo-5-(trifluoromethylthio)-pyrrole and m-chloroperbenzoic acid are used as starting materials, the course of the reaction can be represented by the following equation:

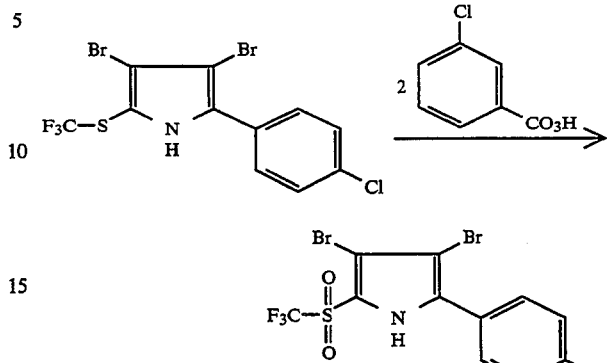

If, according to Process C, 2-(3,4-dichlorophenyl)-3-bromo-5-(chlorodifluoromethylsulphonyl)-pyrrole and chloromethyl ethyl ether are used as starting materials, the course of the reaction can be represented by the following equation:

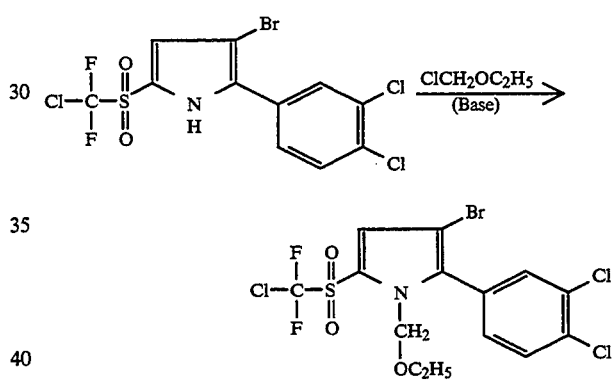

If, according to Process D, 2-(4-chlorophenyl)-3,4-dibromo-5-(difluorochloromethylthio)-pyrrole and chloromethyl ethyl ether are used as starting materials, the course of the reaction can be represented by the following equation:

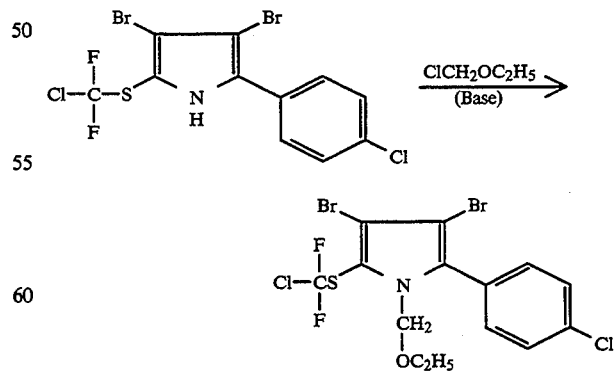

If, according to Process E, 2-(4-chlorophenyl)-5-(difluorochloromethylthio)-pyrrole and bromine are used as starting materials, the course of the reaction can be represented by the following equation:

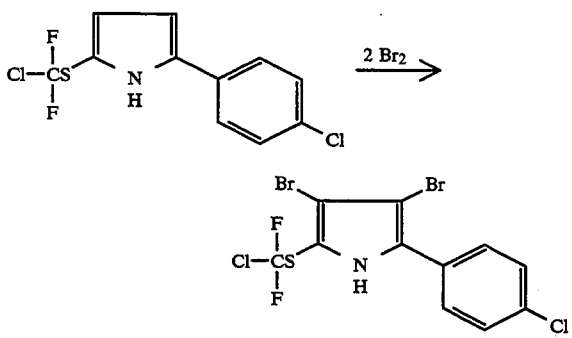

Process A for the preparation of compounds of the formula (Ia) is characterised in that 2-arylpyrroles of the formula (II) are treated with halogenating agents.

Diluents which can be employed in Process A are all customary solvents. The following can preferably be used: hydrocarbons such as benzene and hexane, halogenated hydrocarbons such as chloroform and methylene chloride, furthermore ethers such as dibutyl ether, tetrahydrofuran, dioxane, moreover organic acids such as formic acid and acetic acid. Water can furthermore be used as the diluent.

Halogenating agents which can be employed are all customary halogenating agents. The following are preferably used: chlorine, bromine, sodium hypochlorite, potassium hypochlorite, sodium hypobromite, potassium hypobromite, sulphuryl chloride, t-butyl hypochlorite, N-chlorosuccinimide and N-bromosuccinimide.

The temperatures can be varied within a substantial range. In general, the process is carried out at temperatures from $-10°$ C. to $+120°$ C., preferably between $0°$ C. and $70°$ C.

When carrying out the process, the reactants of the formula (II) are reacted with equimolar amounts, or with an excess, of a halogenating agent.

This reaction is generally carried out under atmospheric pressure. If chlorine and bromine are used, the reaction can also be carried out under elevated pressure (up to 5000 hPa).

Process B for the preparation of compounds of the formula (Ia) is characterised in that 2-arylpyrroles of the formula (III) are reacted with oxidants.

Diluents which can be employed in Process B are all customary solvents. The following can preferably be used: hydrocarbons such as benzene and hexane, halogenated hydrocarbons such as chloroform and methylene chloride, furthermore ethers such as dibutyl ether, tetrahydrofuran, dioxane, moreover organic acids such as formic acid and acetic acid. Water can furthermore be used as the diluent.

Oxidants which can be employed are all customary oxidants. The following are preferably used: m-chloroperbenzoic acid, potassium hydrogen peroxodisulphate (oxone), magnesium monoperoxyphthalate, $H_2O_2$, atmospheric oxygen in the presence of catalysts, potassium permanganate or $CrO_3$.

The temperatures can be varied within a substantial range. In general, the process is carried out at temperatures from $-30°$ C. to $+200°$ C. preferably between $-10°$ C. and $+80°$ C.

When carrying out the process, the reactants of the formula (III) are reacted with one or two equivalents of an oxidant, depending on the desired degree of oxidation of the sulphur. If appropriate, an excess of oxidant can also be employed.

Process C for the preparation of compounds of the formula (Ib) is characterised in that 2-arylpyrroles of the formula (Ia) are reacted with compounds of the formula (IV), if appropriate in the presence of bases and if appropriate in the presence of diluents.

Diluents which are suitable for Process C are all inert organic solvents. These preferably include hydrocarbons such as benzene, toluene, xylene, furthermore ethers such as dibutyl ether, tert.-butyl methyl ether, tetrahydrofuran, dioxane, moreover polar solvents such as dimethyl sulphoxide, acetonitrile, sulpholane, dimethylformamide and N-methyl-pyrrolidone.

Bases which can be employed are all customary proton acceptors. The following can preferably be used: alkali metal oxides, alkali metal hydroxides, alkali metal carbonates, alkaline earth metal oxides, alkaline earth metal hydroxides and alkaline earth metal carbonates such as sodium hydroxide, potassium hydroxide, magnesium oxide, calcium oxide, sodium carbonate, potassium carbonate and calcium carbonate, all of which can also be employed in the presence of phase transfer catalysts such as, for example, triethylbenzylammonium chloride, tetrabutylammonium bromide or 18-crown-6. Alkali metal amides, alkali metal hydrides, alkaline earth metal amides and alkaline earth metal hydrides such as sodium amide, sodium hydride and calcium hydride, and furthermore alkali metal alcoholates, such as sodium methylate, sodium ethylate and potassium tert.-butylate, can also be employed.

When carrying out the process, the reaction temperatures can be varied within a substantial range. In general, the process is carried out at temperatures between $-10°$ C. and $200°$ C., preferably between $0°$ C. and $120°$ C.

When carrying out the process, the reactants of the formula (Ia), the deprotonating bases and the components of the formula (IV) are generally employed in approximately equimolar amounts. However, it is also possible to employ a larger excess (up to 3 mol) of one or the other components.

Process C is generally carried out under atmospheric pressure, but can also be carried out under superatmospheric pressure.

Process D for the preparation of compounds of the formula (Ic) is characterised in that 2-arylpyrroles of the formula (III) are reacted with compounds of the formula (IV), if appropriate in the presence of bases and if appropriate in the presence of diluents.

Diluents which are suitable for Process D are all inert organic solvents. These preferably include hydrocarbons such as benzene, toluene, xylene, furthermore ethers such as dibutyl ether, tert.-butyl methyl ether, tetrahydrofuran, dioxane, moreover polar solvents such as dimethyl sulphoxide, acetonitrile, sulpholane, dimethylformamide and N-methyl-pyrrolidone.

Bases which can be employed are all customary proton acceptors. The following can preferably be used: alkali metal oxides, alkali metal hydroxides, alkali metal carbonates, alkaline earth metal oxides, alkaline earth metal hydroxides and alkaline earth metal carbonates such as sodium hydroxide, potassium hydroxide, magnesium oxide, calcium oxide, sodium carbonate, potassium carbonate and calcium carbonate, all of which can also be employed in the presence of phase transfer catalysts such as, for example, triethylbenzylammonium chloride, tetrabutylammoniumbromide or 18-crown-6.

Alkali metalamides, alkali metal hydrides, alkaline earth metal amides and alkaline earth metal hydrides such as sodium amide, sodium hydride and calcium hydride, and furthermore alkali metal alcoholates, such as sodium methylate, sodium ethylate and potassium tert.-butylate, can also be employed.

When carrying out the process, the reaction temperatures can be varied within a substantial range. In general, the process is carried out at temperatures between −10° C. and 200° C., preferably between 0° C. and 120° C.

When carrying out the process, the reactants of the formula (III), the deprotonating bases and the components of the formula (IV) are generally employed in approximately equimolar amounts. However, it is also possible to employ a larger excess (up to 3 mol) of one or the other components.

The process is generally carried out under atmospheric pressure but can also be carried out under elevated pressure.

Process E for the preparation of compounds of the formula (Id) (=III) is characterised in that 2-arylpyrroles of the formula (V) are treated with halogenating agents.

Diluents which can be employed in Process E are all customary solvents. The following can preferably be used: hydrocarbons such as benzene and hexane, halogenated hydrocarbons such as chloroform and methylene chloride, furthermore ethers such as dibutyl ether, tetrahydrofuran, dioxane, moreover organic acids such as formic acid and acetic acid. Water can furthermore be used as the diluent.

Halogenating agents which can be employed are all customary halogenating agents. The following are preferably used: chlorine, bromine, sodium hypochlorite, potassium hypochlorite, sodium hypobromite, potassium hypobromite, sulphuryl chloride, t-butyl hypochlorite, N-chlorosuccinimide and N-bromosuccinimide.

The temperatures can be varied within a substantial range. In general, the process is carried out at temperatures from −10° C. to +120° C. preferably between 0° C. and 70° C.

When carrying out the process, the reactants of the formula (V) are reacted with equimolar amounts, or with an excess, of a halogenating agent.

This reaction is generally carried out under atmospheric pressure. If chlorine or bromine are used as halogenating agents, the reaction can also be carried out under elevated pressure (up to 5000 hPa).

The starting materials of the general formula (II) required for the preparation of compounds of the general formula (Ia) by Process A are new; they are obtained when 2-arylpyrroles of the formula (V)

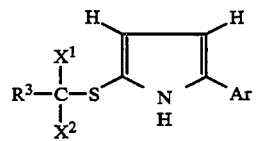 (V)

in which $R^3$, $X^1$, $X^2$ and Ar have the abovementioned meaning are reacted with oxidants.

If, for example, 2-(4-chlorophenyl)-5-(difluorochloromethylthio)-pyrrole and m-chloroperbenzoic acid are used as starting materials, the course of the reaction by this process can be represented by the following equation:

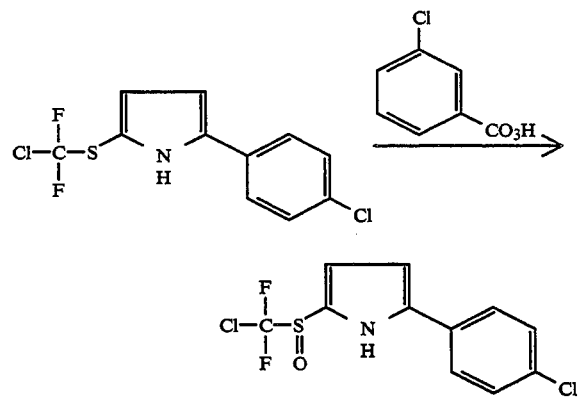

The process for the preparation of compounds of the formula (II) is characterised in that 2-arylpyrroles of the general formula (V) are reacted with oxidants.

Diluents which can be employed in this process are all customary solvents. The following can preferably be used: hydrocarbons such as benzene and hexane, halogenated hydrocarbons such as chloroform and methylene chloride, furthermore ethers such as dibutyl ether, tetrahydrofuran, dioxane, moreover organic acids such as formic acid and acetic acid. Water can furthermore be used as the diluent.

Oxidants which can be employed are all customary oxidants. The following are preferably used: m-chloroperbenzoic acid, potassium hydrogen peroxodisulphate (oxone), magnesium monoperoxyphthalate, $H_2O_2$, atmospheric oxygen in the presence of catalysts, potassium permanganate or $CrO_3$.

The temperatures can be varied within a substantial range. In general, the process is carried out at temperatures from −30° C. to +200° C. preferably between −10° C. and +80° C.

When carrying out the process, the reactants of the formula (V) are reacted with one or two equivalents of an oxidant, depending on the desired degree of oxidation of the sulphur. If appropriate, an excess of oxidant can also be employed.

The starting materials of the formula (V) are new; they are obtained when 2-arylpyrroles of the general formula (VI)

 (VI)

in which Ar has the abovementioned meaning are reacted with sulphenyl chlorides of the general formula (VII)

 (VII)

in which $X^1$, $X^2$ and $R^3$ have the abovementioned meaning, if appropriate in the presence of bases and if appropriate in the presence of diluents.

If, according to this preparation process, 2-(3,4-dichlorophenyl)-pyrrole and trifluoromethylsulphenyl chloride are used as starting materials, the course of the reaction can be represented by the following equation:

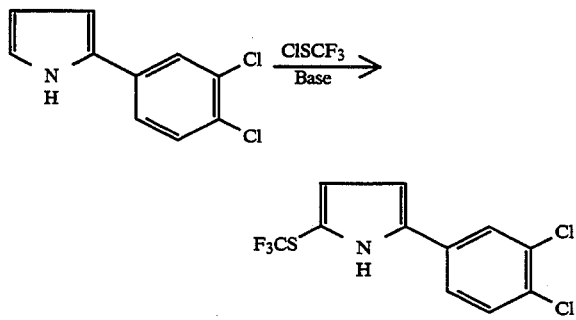

The process for the preparation of compounds of the formula (V) is characterised in that 2-arylpyrroles of the formula (VI) are reacted with sulphenyl chlorides of the general formula (VII), if appropriate in the presence of bases and if appropriate in the presence of diluents.

Diluents which are suitable in this process are all inert organic solvents. These preferably include hydrocarbons such as benzene, toluene, xylene, furthermore ethers such as dibutyl ether, tert.-butyl methyl ether, tetrahydrofuran, dioxane, moreover polar solvents such as dimethyl sulphoxide, acetonitrile, sulpholane, dimethylformamide and N-methyl-pyrrolidone.

Bases which can be employed are, for example, alkali metal amides, alkali metal hydrides, alkaline earth metal amides and alkaline earth metal hydrides such as sodium amide, sodium hydride and calcium hydride, and moreover also alkali metal alcoholates such as sodium methylate, sodium ethylate and potassium tert.-butylate.

When carrying out the process, the reaction temperatures can be varied within a substantial range. In general, the process is carried out at temperatures between −70° C. and +50° C., preferably between −30° C. and +30° C.

When carrying out the process, the reactants of the formulas(VI) and (VII) are employed in equimolar ratios. If appropriate, an excess of the reactants of the formula (VII) can be employed.

The bases which may be employed are generally employed in equimolar amounts, or in a slight excess.

This reaction is generally carried out under atmospheric pressure. If gaseous-sulphenyl chlorides are used, the reaction can also be carried out under elevated pressure (up to 5000 hPa).

The 2-arylpyrroles of the general formula (VI) are known and can be prepared by known processes (compare: A. Gossauer, Die Chemie der Pyrrole [Pyrrole Chemistry], Springer-Verlag, Berlin 1974, p. 276; N. Engel, W. Steglich, Angew. Chemie 90, 719 (1978)).

Some of the sulphenyl chlorides of the general formula (VII) are known and can be prepared by methods known in principle (compare Houben-Weyl, Georg Thieme-Verlag Stuttgart, Vol. 9, p. 267 et seq.; cf. furthermore DE-A 4,036,515).

The substituted 2-arylpyrroles (I) according to the invention are suitable for combating animal pests, in particular insects, arachnids and nematodes, which are encountered in agriculture, in forests, in the protection of stored products and materials and in the field of hygiene, and they are well tolerated by plants and have a favourable toxicity to warm-blooded species. They are active against normally sensitive and resistant species and against all or individual development stages. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tapaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp., Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus*

*sulcatus, Cosmopolites sprdidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., Tenebrio molitor, Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the-Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The substituted 2-arylpyrroles (I) according to the invention are not only active against plant, hygiene and stored product tests, but also, in the veterinary medicine sector, against animal parasites (ectoparasites) such as scaly ticks, argasidae, scab mites, trombidae, flies (stinging and sucking), parasitic fly larvae, lice, hair lice, bird lice and fleas. They are active against normally sensitive and resistant species and strains, as well as against all parasitic and non-parasitic stages of development of the ectoparasites.

The substituted 2-arylpyrroles (I) according to the invention are distinguished by a high insecticidal activity. They can be employed particularly successfully against insects which are harmful to plants, such as, for example, against the larvae of the mustard beetle (*Phaedon cochleariae*), against the green peach aphid (*Myzus persicae*) or against the black bean aphid (*Aphis fabae*). In this context, the active compounds according to the invention display not only protective, but also leaf-acting systemic and root-acting systemic properties.

Besides, the substituted 2-arylpyrroles (I) according to the invention are also suitable for combating soil insects and can be employed, for example, for combating onion maggots (*Phorbia antiqua*) in the soil.

Moreover, the substituted 2-arylpyrroles (I) according to the invention have a powerful action against hygiene and stored product pests and can be employed, for example, for combating the German cockroach (*Blattella germanica*).

Finally, the new active compounds of the formula (i) are also suitable for combating phytopathogenic fungi; for example, the active compounds display an activity against *Pyricularia oryzae,* for example on rice.

The substituted 2-arylpyrroles (I) according to the invention can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the substituted 2-arylpyrroles (I) according to the invention with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The substituted 2-arylpyrroles (I) according to the invention can be present in their commercially available formulations and in the use forms, prepared from these formulations, as a mixture with other active compounds, such as insecticides, attractants, sterilising agents, acaricides, nematicides, fungicides, growth-regulating substances or herbicides. The insecticides include, for example, phosphates, carbamates, carboxylates, chlorinated hydrocarbons, phenylureas, substances produced by microorganisms and the like.

The substituted 2-arylpyrroles (I) according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The substituted 2-arylpyrroles (I) according to the invention are also suitable for combating insects, mites, ticks and the like in the field of animal husbandry and livestock breeding, so that better results, for example higher milk yields, higher weight, more beautiful coat, longer life and the like can be achieved by combating the pests.

The substituted 2-arylpyrroles (I) according to the invention are employed in this field in a known manner, such as by oral administration in the form of, for example, tablets, capsules, drinks, granules, by dermal or external administration, for example in the form of dipping, spraying, pouring-on, spotting-on and dusting, and by parenteral administration, for example in the form of an injection, and furthermore by the feed-through method. An application in the form of shaped articles (collar, ear tag) is also possible.

The examples which follow are intended to illustrate the invention further.

PREPARATION EXAMPLES

Example 1 (Process A)

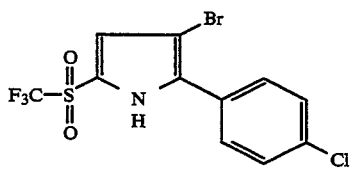

1.9 g (6.1 mmol) of 2-(4-chlorophenyl)-5-(trifluoromethylsulphonyl)-pyrrole are dissolved in 50 ml of chloroform, 2.4 ml (47 mmol) of bromine are added to the solution, and the mixture is stirred for 10 hours at room temperature. The solution is subsequently evaporated in a rotary evaporator, and the product is subjected twice to codistillation with toluene.

Yield: 2.3 g (=97% of theory) of 2-(4-chlorophenyl)-3-bromo-5-(trifluoromethylsulphonyl)-pyrrole;
Physical data, see Table 1.

Example 2 (Process B)

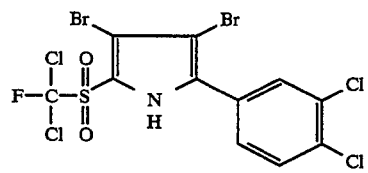

2.86 g (5.7 mmol) of 2-(3,4-dichlorophenyl)-3,4-dibromo-5-(dichlorofluoromethylthio)-pyrrole are dissolved in 35 ml of chloroform and the solution is cooled to −25° C. A solution of 3.6 g of m-chloroperbenzoic acid (55% strength) (11.5 mmol) in 50 ml of chloroform is added dropwise in the course of 8 minutes. Stirring is continued for 5 hours at room temperature. The reaction solution is subsequently washed twice using 50 ml portions of Na$_2$SO$_4$ solution and twice using 50 ml portions of 10% strength Na$_2$CO$_3$ solution. The organic phase is dried over Na$_2$SO$_4$ and evaporated in a rotary evaporator.

Yield: 2.5 g (=87% of theory) of 2-(3,4-dichlorophenyl)-3,4-dibromo-5-(dichlorofluoromethylsulphonyl)-pyrrole;
Physical data, see Table 1.

Example 3 (Process C)

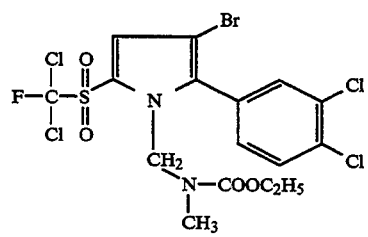

3 g (6.6 mmol) of 2-(3,4-dichlorophenyl)-3-bromo-5-(dichlorofluoromethylsulphonyl)-pyrrole are dissolved in 80 ml of dry tetrahydrofuran, and 0.8 g (6.0 mmol) of potassium tert.-butylate is added to the solution. A solution of 1.1 g (7.2 mmol) of ethyl N-methyl-N-chloromethyl-carbamate, dissolved in tetrahydrofuran, is added dropwise to this mixture. The mixture is stirred for hours at room temperature and then poured into water and extracted using dichloromethane. The mixture is dried over Na$_2$SO$_4$ and then evaporated, and the residue is chromatographed on silica gel (petroleum ether/CH$_2$Cl$_2$32 1:1).

Yield: 1.4 g (=37% of theory) of 1-(N-methyl-ethoxycarbonylamino-methyl) -2- (3,4-dichlorophenyl)-3-bromo-5-(dichlorofluoromethylsulphonyl)pyrrole;
Physical data, see Table 1.

Example 4 (Process D)

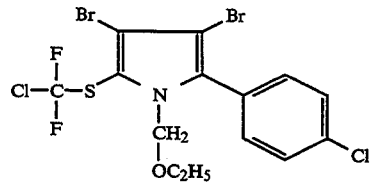

3.0 g (6.64 mmol) of 2-(4-chlorophenyl)-3,4-dibromo-5-(difluorochloromethylthio)-pyrrole are dissolved in 55 ml of dry tetrahydrofuran and 0.78 g (6.9 mmol) of potassium tert.-butylate are added to the solution. 0.69 g (7.3 mmol) of chloromethyl ethyl ether dissolved in ~20 ml of tetrahydrofuran are added dropwise and the mixture is stirred for 19 hours at room temperature. The mixture is subsequently poured into water and extracted using dichloromethane, and the organic phase is washed twice using water. The organic phase is dried over MgSO₄ and evaporated.

Yield: 2.96 g (=87% of theory) of 1-(ethoxymethyl)-2-(4-chlorophenyl)-3,4-dibromo-5-(difluorochloromethyl)-pyrrole;

Physical data, see Table 1.

The compounds of the formula (I) listed in Table 1 below can also be prepared analogously to Examples 1 to 4 and following the above general information on the Preparation Processes A to E according to the invention:

TABLE 1

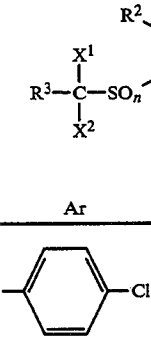

(I)

| Preparation Example No. | $R^1$ | $R^2$ | $R^3$ | $X^1$ | $X^2$ | Ar | $R^4$ | n | Process Variant | Physical Constants |
|---|---|---|---|---|---|---|---|---|---|---|
| 1 | Br | H | F | F | F | 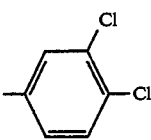 | H | 2 | A | ¹H-NMR(CDCl₃) δ=7.28(1H, d), 7.50(2H, d), 7.65(2H, d), 9.50(1H, br). |
| 2 | Br | Br | F | Cl | Cl | 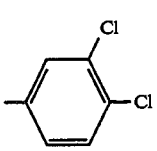 | H | 2 | B | ¹H-NMR(DMSO) δ=7.6-7.8(2H, m), 7.85-8.00(1H, m) 13, 68(1H, br). |
| 3 | Br | H | F | Cl | Cl | 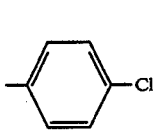 | —CH₂—N(COOC₂H₅)(CH₃) | 2 | C | ¹H-NMR(CDCl₃)δ= 1.10(3H, t), 2.65 (3H, s), 3.80(2H, q) 5.80(2H, s), 7.15 (1H, dd), 7.35(1H, s) 7.40(1H, d), 7.57 (1H, d) |
| 4 | Br | Br | Cl | F | F | 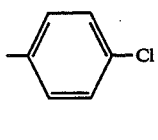 | —CH₂OC₂H₅ | 0 | D | ¹H-NMR(CDCl₃)δ= 1.12(3H, t), 3.40 (2H, q), 5.30(2H, s), 7.45(4H, dd, AB-System). |
| 5 | Br | Br | Cl | Cl | F | 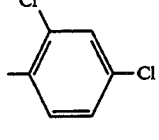 | —CH₂OC₂H₅ | 0 | D | |
| 6 | Br | Br | Cl | Cl | F | 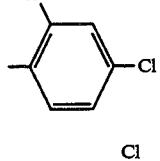 | —CH₂—O—CH(CH₃)₂ | 0 | D | ¹H-NMR(CDCl₃)δ= 1.15(3H, t), 3.45 (2H, q), 5.35(2H, s) 7.35(1H, s)7.48 (4H, dd, AB-System). |
| 7 | Br | Br | Cl | Cl | F | 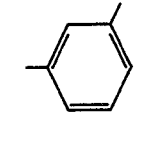 | —CH₂OC₂H₅ | 0 | D | ¹H-NMR(CDCl₃)δ= 1.05(3H, t), 3.25 (2H, q), 5.1, 5.5 (2H, 2x br), 7.25-7.40(4H, m), 7.60 (1H, d). |
| 8 | Br | H | Cl | F | F | (Cl at meta position) | —H | 2 | A | ¹H-NMR(DMSO)δ= 7.45-7.60(3H, m), 7.65-7.80(2H, m), 13.8(1H, br). |

TABLE 1-continued (I)

$$R^3-\underset{X^2}{\overset{X^1}{C}}-SO_n-\underset{\underset{R^4}{N}}{\overset{R^2}{\diagdown}}\overset{R^1}{\diagup}-Ar$$

| Preparation Example No. | R¹ | R² | R³ | X¹ | X² | Ar | R⁴ | n | Process Variant | Physical Constants |
|---|---|---|---|---|---|---|---|---|---|---|
| 9 | Br | H | Cl | F | F | 3-Cl-C₆H₄ | —CH₂OC₂H₅ | 2 | C | ¹H-NMR(CDCl₃)δ= 1.15(3H, t), 3.45 (2H, q), 7.30(1H, s) 7.35–7.55(4H, m). |
| 10 | Br | Br | Cl | Cl | F | 2,4-di-Cl-C₆H₃ | —H | 2 | A | ¹H-NMR(DMSO)δ= 7.5–7.8(3H, m) 13.7(1H, br) |
| 11 | Br | Br | Cl | F | F | 3-Cl-C₆H₄ | —CH₂—OCH(CH₂F)₂ | 0 | D | ¹H-NMR(CDCl₃)δ= 3.7–4.0(1H, m), 4.32 (1H, d), 4.58(1H, d) 5.45(2H, s), 7.24– 7.80(4H, m). |
| 12 | Br | Br | Cl | Cl | F | 3-Cl-C₆H₄ | —CH₂OC₂H₅ | 0 | D | ¹H-NMR(CDCl₃)δ= 1.15(3H, t), 3.40 (2H, q), 5.35(2H, s), 7.25–7.80(4H, m). |
| 13 | Br | Br | Cl | Cl | F | 2-Cl-4-Br-C₆H₃ | —CH₂—N(C(O)OCH₃)CH₂CH(CH₃)₂ | 0 | D | ¹H-NMR(CDCl₃)δ= 0.75(6H, d), 1.60 (1H, dq), 2.50(2H, d) 3.40(3H, s), 5.70 (2H, s), 7.08(1H, dd) 7.40(1H, dd), 7.75 (1H, d). |
| 14 | Br | Br | Cl | Cl | F | 3-Cl-C₆H₄ | —CH₂—N(C(O)OCH₃)CH₂CH(CH₃)₂ | 0 | D | ¹H-NMR(CDCl₃)δ= 0.80(6H, d), 1.60 (1H, dq), 2.50(2H, d) 3.45(3H, s), 5.70 (2H, s), 7.20–7.50 (4H, m). |
| 15 | Br | H | Cl | Cl | F | 3-Cl-C₆H₄ | —H | 2 | A | ¹H-NMR(DMSO)δ= 7.45(1H, s), 7.55 (2H, m), 7.65–7.80 (2H, m), 13.8(1H, br) |
| 16 | Br | H | F | F | Cl | 4-Cl-C₆H₄ | —H | 2 | A | ¹H-NMR(DMSO)δ= 7.45(1H, s), 7.55 (2H, m), 7.65–7.80 (2H, m)13.75(1H, br) |
| 17 | Br | H | Cl | Cl | F | 3-Cl-C₆H₄ | —CH₂OC₂H₅ | 2 | C | ¹H-NMR(CDCl₃)δ= 1.15(3H, t), 3.45 (2H, q), 5.38(2H, s) 7.3–7.6(5H, m). |

TABLE 1-continued $$\text{R}^3-\overset{\overset{X^1}{|}}{\underset{\underset{X^2}{|}}{C}}-SO_n-\underset{\underset{R^4}{|}}{\left[\begin{array}{c}R^2 \quad R^1 \\ \diagdown \diagup \\ N \\ \end{array}\right]}-Ar \quad (I)$$

| Preparation Example No. | R¹ | R² | R³ | X¹ | X² | Ar | R⁴ | n | Process Variant | Physical Constants |
|---|---|---|---|---|---|---|---|---|---|---|
| 18 | Br | H | Cl | F | F | 4-Cl-C₆H₄ | —CH₂OC₂H₅ | 2 | C | ¹H-NMR(CDCl₃)δ= 1.15(3H, t), 3.45 (2H, q), 5.35(2H, s) 7.35(1H, s), 7.48 (4H, AB-System). |
| 19 | Br | H | Cl | F | F | 3,4-Cl₂-C₆H₃ | —H | 2 | A | ¹H-NMR(CDCl₃)δ= 7.20(1H, s), 7.50 (1H, d), 7.68(1H, dd) 7.90(1H, d), 13.1 (1H, br). |
| 20 | Br | H | Cl | Cl | F | 3,4-Cl₂-C₆H₃ | —H | 2 | A | ¹H-NMR(CDCl₃)δ= 7.20(1H, d), 7.50 (1H, d), 7.68(1H, dd) 7.90(1H, d), 13.2 (1H, br). |
| 21 | Br | Br | Cl | Cl | F | 3,4-Cl₂-C₆H₃ | —CH₂OC₂H₅ | 2 | C | ¹H-NMR(CDCl₃)δ= 1.15(3H, t), 3.50 (2H, q), 5.40(2H, s) 7.35(1H, dd), 7.60– 7.80(2H, m) |
| 22 | Br | Br | Cl | Cl | F | 3,5-Cl₂-C₆H₃ | —CH₂OC₂H₅ | 1 | C | ¹H-NMR(CDCl₃)δ= 1.20(3H, t), 3.55 (2H, q), 5.45(2H, s) 7.50(2H, d), 7.60 (1H, d) |
| 23 | Br | H | F | F | F | 4-Cl-C₆H₄ | —H | 1 | A | ¹H-NMR(CDCl₃)δ= 1.30(3H, t), 3.40 (1H, qd), 3.65 (1H, gd), 7.3–7.5 (4H, m). |
| 24 | Br | Br | F | F | F | 4-Cl-C₆H₄ | —H | 2 | B | ¹H-NMR(CDCl₃)δ= 7.52(2H, d), 7.65 (2H, d), 9.6(1H, br) |
| 25 | Br | Br | F | F | F | 4-Cl-C₆H₄ | —H | 1 | B | ¹H-NMR(CDCl₃)δ= 7.48(2H, d), 7.60 (2H, d), 10, 32 (1H, br). |
| 26 | Br | H | Cl | F | F | 3,4-Cl₂-C₆H₃ | —CH₂OC₂H₅ | 2 | C | ¹H-NMR(CDCl₃)δ= 1.15(3H, t), 3.50 (2H, q), 5.35(2H, s) 7.30(1H, s), 7.35 (1H, dd), 7.60(1H, d) 7.67(1H, d). |

TABLE 1-continued

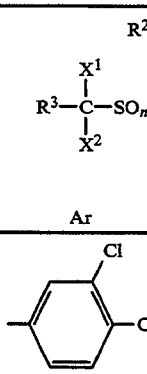

(I)

| Preparation Example No. | R¹ | R² | R³ | X¹ | X² | Ar | R⁴ | n | Process Variant | Physical Constants |
|---|---|---|---|---|---|---|---|---|---|---|
| 27 | Br | H | Cl | Cl | F | 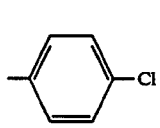 | $-CH_2OC_2H_5$ | 2 | C | $^1$H-NMR(CDCl$_3$)δ= 1.18(3H, t), 3.50 (2H, q), 5.35(2H, s) 7.30(1H, s), 7.35 (1H, dd), 7.60(1H, d) 7.68(1H, d). |
| 28 | Br | H | F | F | F | 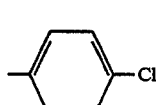 | $-CH_2OC_2H_5$ | 2 | C | $^1$H-NMR(CDCl$_3$)δ= 1.15(3H, t), 3.45 (2H, q), 5.35(2H, s) 7.32(1H, s), 7.40– 7.55(4H, m). |
| 29 | Br | Br | F | F | F | 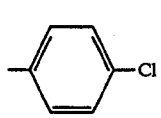 | $-CH_2OC_2H_5$ | 2 | C | $^1$H-NMR(CDCl$_3$)δ= 1.15(3H, t), 3.42 (2H, q), 5.40(2H, s) 7.42(2H, d), 7.52 (2H, d) |
| 30 | Br | Br | F | F | F | 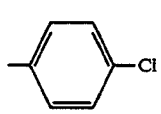 | $-CH_2OC_2H_5$ | 1 | C | $^1$H-NMR(CDCl$_3$)δ= 1.10(3H, t), 3.40 (2H, dq), 5.32(1H, d) 5.55(1H, d), 7.45 (4H, AB-System) |
| 31 | Br | Br | $-CH_3$ | F | F | 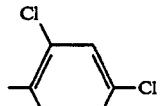 | $-H$ | 2 | B | $^1$H-NMR(DMSO)δ= 2.10(3H, t), 7.5– 7.7(4H, m), 13.6 (1H, s). |
| 32 | Br | H | $-CH_3$ | F | F | 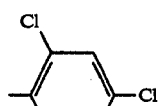 | $-H$ | 2 | A | |
| 33 | Br | H | $-CF_2H$ | F | F | 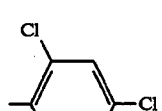 | $-CH_2OC_2H_5$ | 2 | C | $^1$H-NMR(CDCl$_3$)δ= 1.05(3H, t), 3.35 (2H, q), 5.15(1H, d) 5.60(1H, d), 6.3 (1H, tt), 7.25–7.45 (3H, m), 7.60(1H, d) |
| 34 | Br | H | F | Cl | Cl | 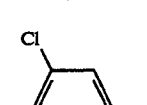 | $-H$ | 2 | A | $^1$H-NMR(DMSO)δ= 7.40(1H, d), 7.55 (2H, m), 7.80(1H, d) 13.8(1H, br). |
| 35 | Br | H | F | Cl | Cl | 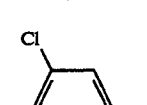 | $-CH_2OC_2H_5$ | 2 | C | $^1$H-NMR(DMSO)δ= 1.10(3H, t), 3.40 (2H, q), 5.20(1H, d) 5.60(1H, d), 7.2–7.6 (4H, m). |
| 36 | Cl | Cl | Cl | F | F | 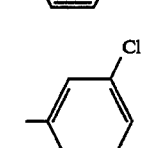 | $-H$ | 2 | A | |

TABLE 1-continued $$\text{(I)}$$

Structure (I): pyrrole with R² and R¹ at 3,4-positions; position 2 bears $-SO_n-C(X^1)(X^2)R^3$; position 5 bears Ar; N bears R⁴.

| Preparation Example No. | R¹ | R² | R³ | X¹ | X² | Ar | R⁴ | n | Process Variant | Physical Constants |
|---|---|---|---|---|---|---|---|---|---|---|
| 37 | Br | H | Cl | Cl | F | 2,4-dichlorophenyl | $-CH_2-N(CH_3)-C(=O)-OC_2H_5$ | 2 | C | |
| 38 | Br | H | Cl | Cl | F | 3-chlorophenyl | $-CH_2-N(CH_3)-C(=O)-OC_2H_5$ | 2 | C | $^1$H-NMR(CDCl$_3$)δ= 1.10(3H, t), 2.60 (3H, s), 3.75(2H, q) 5.80(2H, s), 7.15– 7.50(5H, m). |
| 39 | H | Br | Cl | Cl | F | 2,4,5-trichlorophenyl | $-CH_3$ | 1 | C | |
| 40 | Br | Br | F | F | F | 4-(trifluoromethyl)phenyl | $-CH_2CN$ | 2 | C | |
| 41 | Br | Br | F | F | F | 4-chlorophenyl | H | 0 | E | |
| 42 | Br | Br | F | Cl | Cl | 2,4-dichlorophenyl | H | 0 | E | $^1$H-NMR(CDCl$_3$)δ= 7.38(1H, dd), 7.55 (2H, m), 8.90(1H, br) |
| 43 | Br | Br | F | F | F | 2,4-dichloro-5-fluorophenyl | H | 0 | E | |
| 44 | Br | Br | F | Cl | Cl | 2,4-dichloro-5-(trifluoromethyl)phenyl | H | 0 | E | |
| 45 | Br | Br | Cl | F | F | 3-chlorophenyl | H | 0 | E | $^1$H-NMR(CDCl$_3$)δ= 7.4–7.8(4H, m), 8.8(1H, br). |

TABLE 1-continued (I)

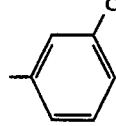

| Preparation Example No. | R¹ | R² | R³ | X¹ | X² | Ar | R⁴ | n | Process Variant | Physical Constants |
|---|---|---|---|---|---|---|---|---|---|---|
| 46 | Br | Br | F | Cl | Cl | 3-Cl-C₆H₄ | H | 0 | E | |
| 47 | Br | Br | F | F | Cl | 4-Cl-C₆H₄ | H | 0 | E | $^1$H-NMR(CDCl$_3$)δ= 7.45(2H, d), 7.60 (2H, d), 8.8(1H, br) |
| 48 | Br | Br | F | Cl | Cl | 3,4-Cl₂-C₆H₃ | H | 0 | E | $^1$H-NMR(CDCl$_3$)δ= 7.5(2H, AB-System) 7.75(1H, d), 8.8 (1H, br), |
| 49 | Br | Br | F | Cl | Cl | 3,5-Cl₂-C₆H₃ | H | 0 | E | $^1$H-NMR(CDCl$_3$)δ= 7.3(1H, d), 7.55 (2H, d), 8.9(1H, br) |
| 50 | Cl | Cl | F | F | F | 4-CF₃-C₆H₄ | H | 0 | E | |
| 51 | Br | H | Cl | F | F | 3-Cl-C₆H₄ | —CH₂N(COOCH₃)(cyclohexyl) | 2 | C | Fp = 111° C. |
| 52 | Br | H | Cl | F | F | 3-Cl-C₆H₄ | —CH₂N(COOC₂H₅)(C₃H₇) | 2 | C | $^1$H-NMR(CDCl$_3$): δ=0.80(3H, t)1.10 (3H, t), 1.30(2H, m), 2.88(2H, dd), 3.75 (2H, q), 5.78(2H, s), 7.1–7.5(5H, m). |
| 53 | Br | H | Cl | F | F | 3-Cl-C₆H₄ | —CH₂N(COOC₂H₅)(CH₃) | 2 | C | Fp = 83° C. |
| 54 | Br | Br | Cl | F | F | 4-Cl-C₆H₄ | —CH₂OC₂H₅ | 2 | C | $^1$H-NMR(CDCl$_3$): δ=1.12(3H, t), 3.45(2H, q), 5.40(2H, s), 7.45(2H, d), 7.50(2H, d). |
| 55 | Br | Br | Cl | F | F | 4-Cl-C₆H₄ | —CH₂N(COOC₂H₅)(CH₃) | 2 | C | $^1$H-NMR(CDCl$_3$): δ=1.10(3H, t), 2.65(3H, s), 3.75(2H, q), 5.85(2H, s), 7.20(2H, d), 7.50(2H, d). |

TABLE 1-continued (I)

structure: pyrrole with R² and R¹ at 3,4 positions; $R^3-C(X^1)(X^2)-SO_n-$ at 2-position; Ar at 5-position; $R^4$ on N

| Preparation Example No. | R¹ | R² | R³ | X¹ | X² | Ar | R⁴ | n | Process Variant | Physical Constants |
|---|---|---|---|---|---|---|---|---|---|---|
| 56 | Br | Br | Cl | F | F | 4-F-C₆H₄ | H | 0 | E | ¹H-NMR(DMSO): δ=7.3(2H, t), 7.7 (2H, dd), 13.0(1H, br). |
| 57 | Br | Br | Cl | F | F | 4-Cl-C₆H₄ | —CH₂N(COOC₂H₅)(C₃H₇) | 2 | C | ¹H-NMR(CDCl₃): δ=0.8(3H, t)1.1 (3H, t), 1.3(2H, m), 2.85(2H, t), 3.75 (2H, q), 5.85(2H, s), 7.20(2H, d), 7.50(2H, d). |
| 58 | Br | Br | Cl | F | F | 4-Cl-C₆H₄ | —CH₂OC₂H₅ | 1 | C | ¹H-NMR(CDCl₃): δ=1.20(3H, t), 3.50 (2H, q), 5.20(2H, s), 7.38 (2H, d), 7.48(2H, d). |
| 59 | Br | Br | Cl | Cl | F | 4-F-C₆H₄ | H | 0 | E | ¹H-NMR(DMSO): δ=7.35(2H, t), 7.70(2H, dd), 13.1(1H, br). |
| 60 | Br | Br | F | F | F | 3-Cl-C₆H₄ | H | 0 | E | ¹H-NMR(DMSO): δ=7.5-7.9(4H, m), 13.2 (1H, br). |
| 61 | Br | Br | Cl | F | F | 3,5-Cl₂-C₆H₃ | H | 0 | E | ¹H-NMR(DMSO): δ=7.65(1H, m), 7.78(2H, m) 13.22(1H, br). |
| 62 | Br | H | Cl | F | F | 2-Cl-C₆H₄ | H | 2 | A | ¹H-NMR(DMSO): δ=7.4-7.7(5H, m) 13, 85(1H, br). |
| 63 | Br | H | Cl | Cl | F | 4-CF₃-C₆H₄ | H | 2 | A | ¹H-NMR(DMSO): δ=7.50(1H, s), 7.70-8.10 (4H, m), 13.9(1H, br). |
| 64 | Br | H | F | F | F | 3-Cl-C₆H₄ | H | 2 | A | ¹H-NMR(DMSO): δ=7.5-7.8(5H, m), 13, 9(1H, br). |
| 65 | Br | H | Cl | Cl | F | 4-F-C₆H₄ | H | 2 | A | ¹H-NMR(DMSO): δ=7.3-7.45(3H, m), 7.75 (2H, dd), 13, 7(1H, br). |

TABLE 1-continued

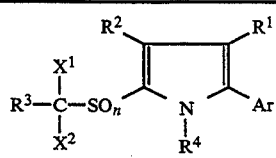

(I)

| Preparation Example No. | R¹ | R² | R³ | X¹ | X² | Ar | R⁴ | n | Process Variant | Physical Constants |
|---|---|---|---|---|---|---|---|---|---|---|
| 66 | Br | H | Cl | Cl | F | 3,5-dichlorophenyl | H | 2 | A | ¹H-NMR(DMSO): δ=7.45(1H, s), 7.70–7.80 (3H, m), 13, 85(1H, br). |
| 67 | Br | H | Cl | F | F | 3,5-dichlorophenyl | H | 2 | A | ¹H-NMR(DMSO): δ=7.50(1H, s), 7.7–7.8 (3H, m), 13.95(1H, br). |
| 68 | Br | H | Cl | F | F | 2,4-dichlorophenyl | H | 2 | A | ¹H-NMR(DMSO): δ=7.55(1H, s), 7.7(1H, d), 7.88(1H, d), 13, 9(1H, br). |
| 69 | Br | H | Cl | F | F | 4-fluorophenyl | H | 2 | A | ¹H-NMR(DMSO): δ=7.35(2H, t), 7.48(1H, s), 7, 75(2H, dd), 13, 75(1H, br). |
| 70 | Br | H | Cl | Cl | F | 2,4-dichlorophenyl | H | 2 | A | ¹H-NMR(DMSO): δ=7.50(1H, s), 7.70(1H, d), 7.90(1H, d), 13.80(1H, br). |
| 71 | Br | Br | Cl | F | F | 3,5-dichlorophenyl | H | 2 | B | ¹H-NMR(DMSO): δ=7.8(3H, m), 13, 8(1H, br). |
| 72 | Br | Br | Cl | F | F | 4-fluorophenyl | H | 2 | B | ¹H-NMR(DMSO): δ=7.4(2H, t), 7.75 (2H, dd), 13, 8(1H, br). |
| 73 | Br | Br | F | F | F | 3-chlorophenyl | H | 2 | B | ¹H-NMR(DMSO): δ=7.5–7.9(4H, m), 13, 9(1H, br). |
| 74 | Br | Br | Cl | Cl | F | 4-fluorophenyl | H | 2 | B | ¹H-NMR(DMSO): δ=7.35(2H, t), 7.75 (2H, dd), 14, 05(1H, br). |

TABLE 1-continued (I)

$$R^3-\underset{X^2}{\overset{X^1}{C}}-SO_n-\text{[pyrrole with } R^2, R^1, Ar, R^4\text{]}$$

| Preparation Example No. | $R^1$ | $R^2$ | $R^3$ | $X^1$ | $X^2$ | Ar | $R^4$ | n | Process Variant | Physical Constants |
|---|---|---|---|---|---|---|---|---|---|---|
| 75 | Br | H | Cl | F | F | 2-Cl-C₆H₄ | —CH₂OC₂H₅ | 2 | C | $^1$H-NMR(CDCl$_3$): δ=1.05(3H, t), 3.35(2H, q), 5,15(1H, d), 5.60(1H, d), 7.3–7.6(5H, m). |
| 76 | Br | H | Cl | F | F | 2-Cl-C₆H₄ | —CH₂N(CH₃)COOC₂H₅ | 2 | C | $^1$H-NMR(CDCl$_3$): δ=1.1(3H, t), 2.7(3H, s), 3.75(2H, q), 5,75(2H, s), 7.2–7.6(5H, m). |
| 77 | Br | H | Cl | Cl | F | 4-CF₃-C₆H₄ | —CH₂N(CH₃)COOC₂H₅ | 2 | C | $^1$H-NMR(CDCl$_3$): δ=1.1(3H, t), 2.65(3H, s), 3.70(2H, q), 5, 80(2H, s), 7.2–7.6(5H, m). |
| 78 | Br | H | Cl | Cl | F | 4-CF₃-C₆H₄ | —CH₂OC₂H₅ | 2 | C | $^1$H-NMR(CDCl$_3$): δ=1.15(3H, t), 3.50(2H, q), 5.35(2H, s), 7.38(1H, s), 7.60–7.90(4H, m). |
| 79 | Br | H | F | F | F | 3-Cl-C₆H₄ | —CH₂N(CH₃)COOC₂H₅ | 2 | C | $^1$H-NMR(CDCl$_3$): δ=1.1(3H, t), 2.60(3H, s), 3.80(2H, q), 5.78(2H, s), 7.2–7.5(5H, m). |
| 80 | Br | H | F | F | F | 3-Cl-C₆H₄ | —CH₂OC₂H₅ | 2 | C | $^1$H-NMR(CDCl$_3$): δ=1.15(3H, t), 3.45 (2H, q), 5, 35(2H, s), 7.3–7.6 (5H, m). |
| 81 | Br | H | Cl | Cl | F | 4-F-C₆H₄ | —CH₂N(CH₃)COOC₂H₅ | 2 | C | $^1$H-NMR(CDCl$_3$): δ=1.1(3H, t), 2.6(3H, s), 3, 75(2H, q), 5.75(2H, s), 7.10–7.4(5H, m). |
| 82 | Br | H | Cl | Cl | F | 4-F-C₆H₄ | —CH₂OC₂H₅ | 2 | C | $^1$H-NMR(CDCl$_3$): δ=1.15(3H, t), 3.48(2H, q), 5.38(2H, s), 7.20(2H, t), 7.35(1H, s), 7, 50(2H, dd). |
| 83 | Br | H | Cl | Cl | F | 2,4-Cl₂-C₆H₃ | —CH₂N(CH₃)COOC₂H₅ | 2 | C | $^1$H-NMR(CDCl$_3$): δ=1.15(3H, t), 2.65(3H, s), 3.80(2H, q), 5, 80(2H, s), 7.20(2H, d), 7.38(1H, s) 7.48(1H, d). |
| 84 | Br | H | Cl | Cl | F | 2,4-Cl₂-C₆H₃ | —CH₂OC₂H₅ | 2 | C | $^1$H-NMR(CDCl$_3$): δ=1.15(3H, t), 3.50(2H, q), 5.35(2H, s), 7.35(1H, s), 7.45(2H, d), 7.50(1H, d). |

TABLE 1-continued

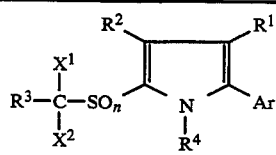

(I)

| Preparation Example No. | R¹ | R² | R³ | X¹ | X² | Ar | R⁴ | n | Process Variant | Physical Constants |
|---|---|---|---|---|---|---|---|---|---|---|
| 85 | Br | H | Cl | F | F | 2,4-dichlorophenyl | $-CH_2N(COOC_2H_5)(CH_3)$ | 2 | C | $^1$H-NMR(CDCl$_3$): $\delta$=1.10(3H, t), 2.65(3H, s), 3.80(2H, q), 5.65(2H, s), 7.20(2H, d), 7, 35(1H, s), 7.48(1H, d). |
| 86 | Br | H | Cl | F | F | 2,4-dichlorophenyl | $-CH_2OC_2H_5$ | 2 | C | $^1$H-NMR(CDCl$_3$): $\delta$=1.20(3H, t), 3.50 (2H, q), 5, 30(2H, q), 7.30 (1H, s), 7.45–7.50(3H, m). |
| 87 | Br | H | Cl | F | F | 2,3-dichlorophenyl | $-CH_2N(COOC_2H_5)(CH_3)$ | 2 | C | $^1$H-NMR(CDCl$_3$): $\delta$=1.20(3H, t), 2.80(3H, s), 3, 85(2H, q), 5.68(2H, AB-System), 7.41(1H, s), 7.43(1H, d), 7.55 (1H, d). |
| 88 | Br | H | Cl | F | F | 2,3-dichlorophenyl | $-CH_2OC_2H_5$ | 2 | C | $^1$H-NMR(CDCl$_3$): $\delta$=1.1(3H, t), 3.5(2H, q), 5.4(2H, d), 7.38(1H, s), 7.40(1H, d), 7, 60(1H, d). |
| 89 | Br | H | Cl | F | F | 4-fluorophenyl | $-CH_2N(COOC_2H_5)(CH_3)$ | 2 | C | $^1$H-NMR(CDCl$_3$): $\delta$=1.1(3H, t), 2.60(3H, s), 3.75(2H, q), 5, 75(2H, s), 7.1–7.4(5H, m). |
| 90 | Br | H | Cl | F | F | 4-fluorophenyl | $-CH_2OC_2H_5$ | 2 | C | $^1$H-NMR(CDCl$_3$): $\delta$=1.12(3H, t), 3.45 (2H, q), 5, 32(2H, s), 7.20 (2H, t), 7.32(1H, s), 7.48 (2H, dd). |
| 91 | Br | Br | Cl | F | F | 4-fluorophenyl | $-CH_2OC_2H_5$ | 2 | C | $^1$H-NMR(CDCl$_3$): $\delta$=1.12(3H, t), 3.42(2H, q), 5.35(2H, s), 7.20(2H, t), 7.22(1H, s), 7, 50(2H, dd). |
| 92 | Br | H | Cl | Cl | F | 2,3-dichlorophenyl | $-CH_2N(COOC_2H_5)(CH_3)$ | 2 | C | $^1$H-NMR(CDCl$_3$): $\delta$=1.20(3H, t), 2.82(3H, s), 3.85(2H, q), 5, 70(2H, AB-System), 7, 38(1H, s), 7.40(1H, d), 7.55(1H, d). |
| 93 | Br | H | Cl | Cl | F | 2,3-dichlorophenyl | $-CH_2OC_2H_5$ | 2 | C | $^1$H-NMR(CDCl$_3$): $\delta$=1.1(3H, t)3, 5(2H, q), 5.42(2H, s), 7.35(1H, s)7.40 (1H, d), 7.58(1H, d). |

TABLE 1-continued (I)

Structure: R³-C(X¹)(X²)-SO_n- attached to pyrrole ring with R² and R¹ at 3,4-positions, Ar at 5-position, and R⁴ on N.

| Preparation Example No. | R¹ | R² | R³ | X¹ | X² | Ar | R⁴ | n | Process Variant | Physical Constants |
|---|---|---|---|---|---|---|---|---|---|---|
| 94 | Br | Br | F | F | F | 4-Cl-phenyl (3-Cl) | —CH₂N(COOC₂H₅)(CH₃) | 2 | C | |
| 95 | Br | Br | Cl | Cl | F | 4-F-phenyl | —CH₂N(COOC₂H₅)(CH₃) | 2 | C | ¹H-NMR(CDCl₃): δ=1.05(3H, t), 2.60(3H, s), 3, 75(2H, q), 5.85(2H, s), 7.15–7.30(4H, AB-System). |
| 96 | Br | Br | Cl | Cl | F | 4-F-phenyl | —CH₂OC₂H₅ | 2 | C | ¹H-NMR(CDCl₃): δ=1.15(3H, t), 3.45 (2H, q), 5, 40(2H, s), 7.22 (2H, t), 7.45(2H, dd). |
| 97 | Br | Br | Cl | Cl | F | 2,4-diCl-phenyl | H | 0 | E | ¹H-NMR(DMSO): δ=7.60(3H, m), 13.10(1H, br). |
| 98 | Br | Br | Cl | Cl | F | 2,4-diCl-phenyl | H | 2 | B | ¹H-NMR(DMSO): δ=7.65(3H, m), 14.15(1H, br). |
| 99 | Br | H | Cl | Cl | F | 2,4-diCl-phenyl | H | 2 | A | ¹H-NMR(DMSO): δ=7.42(1H, s)7, 65(3H, m) 13, 8(1H, br). |
| 100 | Br | H | Cl | Cl | F | 2,4-diCl-phenyl | —CH₂OC₂H₅ | 2 | C | ¹H-NMR(CDCl₃): δ=1.1(3H, t), 3.40(2H, q), 5.2(1H, d)5.6(1H, d), 7.25–7.5(4H, m). |
| 101 | Br | H | Cl | Cl | F | 2,4-diCl-phenyl | —CH₂N(COOC₂H₅)(CH₃) | 2 | C | ¹H-NMR(CDCl₃): δ=1.20(3H, t), 2.70(3H, s), 3, 80(2H, q), 5.75(2H, AB-System), 7.1–7.5(4H, m). |
| 102 | Br | Br | Cl | Cl | F | 2,4-diCl-phenyl | —CH₂OC₂H₅ | 2 | C | ¹H-NMR(CDCl₃): δ=1.1(3H, t), 3.42 (2H, q), 5, 2(1H, d), 5.7 (1H, d), 7.35–7.50(3H, m). |

TABLE 1-continued (I)

$$R^3-\underset{X^2}{\overset{X^1}{C}}-SO_n\underset{R^4}{\overset{R^2}{\underset{N}{\bigvee}}}\overset{R^1}{\underset{Ar}{\bigvee}}$$

| Preparation Example No. | $R^1$ | $R^2$ | $R^3$ | $X^1$ | $X^2$ | Ar | $R^4$ | n | Process Variant | Physical Constants |
|---|---|---|---|---|---|---|---|---|---|---|
| 103 | Br | Br | Cl | Cl | F | 2,4-dichlorophenyl | $-CH_2N(CH_3)COOC_2H_5$ | 2 | C | $^1$H-NMR(CDCl$_3$): δ=1.2(3H, t), 2.75(3H, s), 3.80(2H, q), 5.85(2H, s), 7.2–7.5(3H, m). |
| 104 | Br | Br | Cl | Cl | F | 2,6-difluorophenyl | H | 0 | E | $^1$H-NMR(DMSO): δ=7.25(1H, m), 7.65(2H, m) 13.2(1H, br). |
| 105 | Br | H | Cl | Cl | F | 2,6-difluorophenyl | H | 2 | A | $^1$H-NMR(DMSO): δ=7.28(2H, m), 7.48(1H, d), 7.55–7.75(1H, m), 13.95(1H, br). |
| 106 | Br | H | Cl | F | F | 2,6-difluorophenyl | H | 2 | A | $^1$H-NMR(DMSO): δ=7.3(2H, m), 7.55(1H, s), 7.6–7.7(1H, m)14.02(1H, br). |
| 107 | Br | H | Cl | Cl | F | 2,4-dichlorophenyl | $-CH_2N\text{(2-oxo-1,3-oxazolidin-3-yl)}$ | 2 | C | $^1$H-NMR(CDCl$_3$): δ=3.50(2H, dd), 4.25(2H, dd), 5, 7(2H, s), 7.22(2H, d), 7.38(1H, s), 7.55(1H, d). |
| 108 | Br | H | Cl | Cl | F | 2,4-dichlorophenyl | $-CH_2OCH_2C\equiv CH$ | 2 | C | $^1$H-NMR(CDCl$_3$): δ=2.40(1H, t), 4.22(2H, d), 5.50(2H, s), 7.38(1H, s), 7.45(2H, m), 7.52(1H, m). |
| 109 | Br | H | Cl | Cl | F | 2,4-dichlorophenyl | $-CH_2OC_3H_7$ | 2 | C | $^1$H-NMR(CDCl$_3$): δ=0.90(3H, t), 1.55(2H, m), 3.40(2H, q), 5.35(2H, s), 7.35 (1H, s), 7.45(2H, m), 7.50(1H, m). |
| 110 | Br | H | Cl | Cl | F | 2,4-dichlorophenyl | $-CH_2N(CH_3)COOCH_3$ | 2 | C | $^1$H-NMR(CDCl$_3$): δ=2.65(3H, s), 3.50(3H, s), 5.80(2H, s), 7.2–7.5(4H, m). |

TABLE 1-continued

Structure (I):

$$R^3-\underset{X^2}{\overset{X^1}{C}}-SO_n\text{-[pyrrole with } R^2, R^1, Ar, R^4\text{]}$$

| Preparation Example No. | R¹ | R² | R³ | X¹ | X² | Ar | R⁴ | n | Process Variant | Physical Constants |
|---|---|---|---|---|---|---|---|---|---|---|
| 111 | Br | H | Cl | Cl | F | 2,6-difluorophenyl | —CH₂OC₂H₅ | 2 | C | ¹H-NMR(CDCl₃): δ=1.05(3H, t), 3.35(2H, q), 5.50(2H, s), 7.10(2H, m), 7.38(1H, s), 7.50(1H, m). |
| 112 | Br | H | Cl | F | F | 2,4-dichlorophenyl | —CH₂—N(oxazolidinone) | 2 | C | ¹H-NMR(CDCl₃): δ=3.50(2H, dd), 4.25(2H, dd), 5,68(2H, s), 7.22(2H, d), 7.45(1H, s), 7.55(1H, m). |
| 113 | Br | Br | F | F | F | 2,4-dichlorophenyl | H | 0 | E | ¹H-NMR(DMSO): δ=7.6–7.8(3H, m), 13.1(1H, br). |
| 114 | Br | H | Cl | F | F | 2,4-dichlorophenyl | —CH₂OCH₂C≡CH | 2 | C | Fp = 98° C. |
| 115 | Br | H | Cl | F | F | 2,4-dichlorophenyl | —CH₂OC₃H₇ | 2 | C | Fp = 74° C. |
| 116 | Br | H | Cl | F | F | 2,4-dichlorophenyl | —CH₂OC₄H₉ | 2 | C | ¹H-NMR(CDCl₃: δ=0.90(3H, t), 1.3(2H, m), 1.5(2H, m), 3.45(2H, t), 5.35(2H, s), 7.34(1H, s), 7.40(1H, dd), 7.55 (1H, d), 7.65(1H, d). |
| 117 | Br | H | Cl | F | F | 2,4-dichlorophenyl | —CH₂OCH(CH₃)₂ | 2 | C | Fp = 122° C. |
| 118 | Br | H | Cl | F | F | 2,4-dichlorophenyl | —CH₂OCH₂CH(CH₃)₂ | 2 | C | Fp = 75° C. |
| 119 | Br | H | Cl | Cl | F | 2,4-dichlorophenyl | —CH₂OCH₂C≡CH | 2 | C | Fp = 99° C. |

TABLE 1-continued $$\text{(I)}$$

Structure (I): pyrrole with R² at 3-position, R¹ at 4-position, Ar at 5-position (next to N-R⁴), and at 2-position $R^3-C(X^1)(X^2)-SO_n-$ substituent.

| Preparation Example No. | R¹ | R² | R³ | X¹ | X² | Ar | R⁴ | n | Process Variant | Physical Constants |
|---|---|---|---|---|---|---|---|---|---|---|
| 120 | Br | H | Cl | Cl | F | 3,4-dichlorophenyl | —CH₂OC₄H₉ | 2 | C | Fp = 145° C. |
| 121 | Br | H | Cl | Cl | F | 3,4-dichlorophenyl | —CH₂OCH(CH₃)₂ | 2 | C | ¹H-NMR(CDCl₃): δ=1.1(6H, d), 3.75 (1H, m), 5.35(2H, s), 7.32(1H, s), 7.40(1H, dd), 7.60(1H, d), 7.70(1H, d). |
| 122 | Br | H | Cl | Cl | F | 3,4-dichlorophenyl | —CH₂OCH₂CH(CH₃)₂ | 2 | C | Fp = 102° C. |
| 123 | Br | H | Cl | Cl | F | 3,4-dichlorophenyl | —CH₂OC₃H₇ | 2 | C | Fp = 106° C. |
| 124 | Br | H | Cl | F | F | 3,4-dichlorophenyl | —CH₂NHCOCH₃ | 2 | C | ¹H-NMR(CDCl₃): δ=1.92(3H, s), 5.4 (2H, d), 6, 75(1H, t), 7.28 (1H, dd), 7.35(1H, s), 7.50 (1H, d), 7.62(1H, d). |
| 125 | Br | H | Cl | Cl | F | 3,4-dichlorophenyl | —CH₂NHCOCH₃ | 2 | C | ¹H-NMR(CDCl₃): δ=1.90(3H, s), 5.40(2H, d), 6.80(1H, t), 7.25(1H, dd), 7.35(1H, s), 7.48(1H, d), 7.62(1H, d). |
| 126 | Cl | Cl | Cl | Cl | F | 3,4-dichlorophenyl | H | 0 | E | ¹H-NMR(DMSO): δ=7.75(2H, AB-System), 8.0(1H, s), 13.55(1H, br). |
| 127 | Br | H | Cl | F | F | 2,4-dichlorophenyl | —CH₂O(CH₂)₄Cl | 2 | C | ¹H-NMR(CDCl₃): δ=1, 6-1, 9(4H, m), 3.4–3.6 (4H, m), 5.32(2H, s), 7.32(1H, s), 7.45(2H, m), 7.55(1H, m). |
| 128 | Br | Br | Cl | F | F | 2,4-dichlorophenyl | —CH₂O(CH₂)₄Cl | 2 | C | ¹H-NMR(CDCl₃): δ=1, 6-1, 9(4H, m), 3.4–3.6 (4H, m), 5, 35(2H, s), 7.45 (2H, d)7.55(1H, d). |

TABLE 1-continued (I)

| Preparation Example No. | R¹ | R² | R³ | X¹ | X² | Ar | R⁴ | n | Process Variant | Physical Constants |
|---|---|---|---|---|---|---|---|---|---|---|
| 129 | Br | H | Cl | Cl | F | 2,4-dichlorophenyl | —CH₂O(CH₂)₄Cl | 2 | C | $^1$H-NMR(CDCl₃): δ=1, 65–1.90(4H, m), 3.45–3.55(4H, m), 5.35(2H, s), 7.35(1H, s), 7.43(2H, d), 7.52(1H, d). |
| 130 | Cl | Cl | Cl | F | F | 2,4-dichlorophenyl | H | 0 | E | $^1$H-NMR(DMSO): δ=7.65(1H, m), 7.80(2H, m), 13.15(1H, br). |
| 131 | Cl | Cl | Cl | Cl | F | 2,4-dichlorophenyl | H | 0 | E | $^1$H-NMR(DMSO): δ=7.65(1H, m), 7.78(2H, m), 13.15(1H, br). |
| 132 | Cl | Cl | Cl | Cl | F | 2,3-dichlorophenyl | —CH₂OC₂H₅ | 2 | C | $^1$H-NMR(CDCl₃): δ=1.18(3H, t), 3.50(2H, q) 5.38(2H, s), 7.38(1H, dd), 7.60(1H, d), 7.68(1H, d). |
| 133 | Cl | Cl | Cl | F | F | 2,4-dichlorophenyl | —CH₂OC₂H₅ | 0 | D | $^1$H-NMR(CDCl₃): δ=1,2(3H, t), 3.45(2H, q), 5.3(2H, s), 7.45(3H, m). |
| 134 | Cl | Cl | Cl | F | F | 2,4-dichlorophenyl | H | 2 | B | $^1$H-NMR(DMSO): δ=7, 75(1H, m), 7, 82(2H, m), 13, 8(1H, br). |
| 135 | Cl | Cl | Cl | Cl | F | 2,4-dichlorophenyl | H | 2 | B | $^1$H-NMR(DMSO): δ=7.76(1H, m), 7.85 (2H, m), 13, 78(1H, br). |
| 136 | Cl | Cl | Cl | Cl | F | 2,4-dichlorophenyl | —CH₂OC₂H₅ | 2 | C | $^1$H-NMR(CDCl₃): δ=1.2(3H, t), 3.50(2H, q), 5.35(2H, s), 7.48(2H, m), 7.52(1H, m). |

TABLE 1-continued

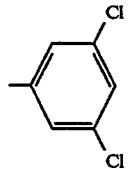

(I)

| Preparation Example No. | R¹ | R² | R³ | X¹ | X² | Ar | R⁴ | n | Process Variant | Physical Constants |
|---|---|---|---|---|---|---|---|---|---|---|
| 137 | Cl | Cl | Cl | F | F | 2,4-dichlorophenyl | —CH$_2$OC$_2$H$_5$ | 2 | C | $^1$H-NMR(CDCl$_3$): δ=1.20(3H, t), 3.52(2H, q) 5.32(2H, s), 7.3–7.5(3H, m). |

PREPARATION OF THE PRECURSORS

Example V-1

10 g (0.057 mol) of 2-(3-chlorophenyl)-pyrrole are dissolved in 50 ml of dry ether, and 6.0 g (0.057 mol) of Na$_2$CO$_3$ are added. The mixture is cooled to −20° C., and a solution of 6.6 ml (0.0627 mol) of chlorodifluoromethylsulphenyl chloride in 20 ml of ether is slowly added dropwise. The mixture is stirred for 2.5 hours at this temperature, and solids are filtered off and washed with ether. The filtrate is washed with water, dried over MgSO$_4$ and evaporated.

The (dark blue) crude product is purified by filtration over silica gel (CH$_2$CH$_2$/petroleum ether=1:1).

Yield: 10.1 g (=61% of theory) of 2-(3-chlorophenyl)-5-(chlorodifluoromethylthio)-pyrrole;
Physical data, see Table 2.

The precursors of the formula (V) mentioned in Table 2 below are also prepared analogously.

TABLE 2

(V)

| Preparation Example No. | R³ | X¹ | X² | Ar | Physical Constants |
|---|---|---|---|---|---|
| V-1 | F | F | Cl | 3-chlorophenyl | $^1$H-NMR(CDCl$_3$), δ=6.55 (1H, dd), 6.72(1H, dd)7.20–7.5(4H, m), 8.6(1H, br) |
| V-2 | F | Cl | Cl | 2,4-dichlorophenyl | $^1$H-NMR(CDCl$_3$), δ=6.60 (1H, dd), 6.75(1H, dd), 7.25 (1H, dd), 7.40–7.50(2H, m), 9.20(1H, br). |
| V-3 | F | Cl | Cl | 2,4-dichlorophenyl | $^1$H-NMR(CDCl$_3$), δ=6.60 (1H, dd), 6.75(1H, dd), 7.2–7.4(3H, m), 8.70(1H, br). |
| V-4 | F | Cl | Cl | 2,3-dichlorophenyl | $^1$H-NMR(CDCl$_3$), δ=6.60 (1H, dd), 6.75(1H, dd), 7.32 (1H, dd), 7.45(1H, d), 7.58 (1H, d), 8.65(1H, br). |
| V-5 | Cl | F | Cl | 3-chlorophenyl | $^1$H-NMR(DMSO)δ=6.72(1H, m) 6.80(1H, m), 7.25–7.50(2H, m) 7.75(1H, dt), 7.90(1H, t), 12.3(1H, br). |

TABLE 2-continued $$R^3-\underset{X^2}{\overset{X^1}{C}}-S-\underset{\underset{H}{N}}{\overset{H}{\underset{\|}{C}}}\overset{H}{\underset{\|}{C}}-Ar \quad (V)$$

| Preparation Example No. | R³ | X¹ | X² | Ar | Physical Constants |
|---|---|---|---|---|---|
| V-6 | Cl | F | F | 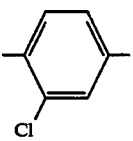 | $^1$H-NMR(CDCl$_3$)δ=6.60 (1H, dd), 6.70(1H, dd), 7.25 (1H, dd), 7.40(2H, m), 9.10 (1H, br). |
| V-7 | F | F | Cl | 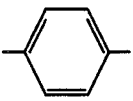 | $^1$H-NMR(DCDl$_3$)δ=6.50 (1H, dd), 7.70(1H, dd), 7.45 (4H, AB-System), 8.50(1H, br) |
| V-8 | F | F | F | 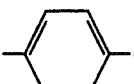 | $^1$H-NMR(DMSO)δ=6.70(2H, m) 7.45(2H, d), 7.80(2H, d), 12.25(1H, br). |
| V-9 | —CH$_3$ | F | F | 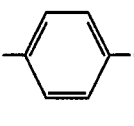 | $^1$H-NMR(DMSO)δ=1.9(3H, t) 6.49(1H, dd), 6.58(1H, dd), 7.35(4H, AB-System), 8.50 (1H, br). |
| V-10 | —CF$_2$H | F | F | 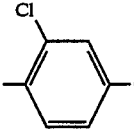 | $^1$H-NMR(CDCl$_3$)δ=5.8(1H, tt, J$_1$=50Hz), 6.60(1H, dd), 6.68 (1H, dd), 7.25(1H, dd), 7.4– 7.5(2H, m), 9.10(1H, br). |

Example II-1

4.5 g (13.2 mmol) of 2-(3-chlorophenyl)-5-(dichlorofluoromethylthio)-pyrrole (V-5) are dissolved in 45 ml of methylene chloride and cooled to −10° C. 8.29 g (26.4 mmol) of 55% strength m-chloroperbenzoic acid, dissolved in 70 ml of CHCl$_3$, are added in the course of one hour, and the mixture is stirred for 3 hours at room temperature.

The mixture is washed twice using 50 ml portions of Na$_2$SO$_4$ solution and twice using 50 ml portions of Na$_2$CO$_3$ solution, dried over Na$_2$SO$_4$ and evaporated.

Yield: 3.96 g (=91% of theory) of 2-(3-chlorophenyl)-5-(dichlorofluoromethylsulphonyl)-pyrrole;

Physical data, see Table 3.

The precursors of the formula (II) mentioned in Table 3 below are also prepared analogously.

TABLE 3

$$R^3-\underset{X^2}{\overset{X^1}{C}}-SO_n-\underset{\underset{H}{N}}{\overset{H}{\underset{\|}{C}}}\overset{H}{\underset{\|}{C}}-Ar \quad (II)$$

| Preparation Example No. | R³ | X¹ | X² | Ar | n | Physical Constants |
|---|---|---|---|---|---|---|
| II-1 | Cl | Cl | F | 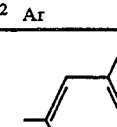 | 2 | $^1$H-NMR(DMSO), δ=7.00 (1H, m), 7.25(1H, m), 7.35– 7.50(2H, m), 7.85(1H, m), 8.10(1H, m), 13,25(1H, br) |
| II-2 | F | Cl | F | 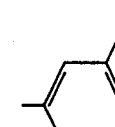 | 2 | $^1$H-NMR(DMSO), δ=7.05 (1H, d), 7.30(1H, d), 7.4– 7.5(2H, m), 7.85(1H, m), 8.10(1H, m), 13.3(1H, br) |

TABLE 3-continued

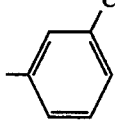
(II)

| Preparation Example No. | R³ | X¹ | X² | Ar | n | Physical Constants |
|---|---|---|---|---|---|---|
| II-3 | F | Cl | F | 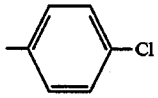 3-Cl-C₆H₄ | 1 | ¹H-NMR(DMSO)δ=6.95 (1H, d), 7.10(1H, d), 7.35–7.50(2H, m), 7.8(1H, m), 8.0(1H, m), 12.8(1H, br) |
| II-4 | F | F | Cl | 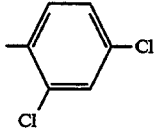 4-Cl-C₆H₄ | 2 | ¹H-NMR(DMSO), δ=7.0(1H, d), 7.35(1H, d), 7.55 (2H, d), 7.95(2H, d), 13.3 (1H, br) |
| II-5 | Cl | Cl | F | 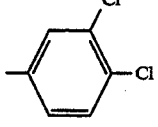 2,4-diCl-C₆H₃ | 1 | |
| II-6 | F | Cl | Cl | 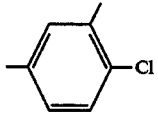 3,4-diCl-C₆H₃ | 2 | ¹H-NMR(DMSO), δ=7.05 (1H, m), 7.25(1H, m), 7.68 (1H, d), 7.90(1H, dd), 8.28 (1H, d), 13.28(1H, br) |
| II-7 | F | F | Cl | 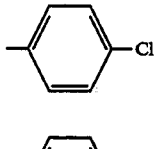 3,4-diCl-C₆H₃ | 2 | ¹H-NMR(DMSO), δ=7.05 (1H, d), 7.30(1H, d), 7.70 (1H, d), 7.88(1H, dd), 8.28 (1H, d), 13.35(1H, br) |
| II-8 | F | F | F | 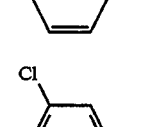 4-Cl-C₆H₄ | 2 | ¹H-NMR(CDCl₃), δ=6.70 (1H, m), 7.25(1H, m), 7.45 (2H, d), 7.55(2H, d), 9.7 (1H, br) |
| II-9 | F | F | F | 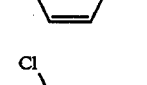 4-Cl-C₆H₄ | 1 | ¹H-NMR(CDCl₃), δ=6.60 (1H, m), 6.90(1H, m), 7.40 (2H, d), 7.55(2H, d), 10.3 (1H, br) |
| II-10 | CF₂H | F | F | 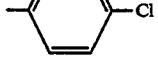 2,4-diCl-C₆H₃ | 2 | |
| II-11 | Cl | Cl | F | 2,4-diCl-C₆H₃ | 2 | |
| II-12 | —CF₂H | F | F |  2,4-diCl-C₆H₃ | 1 | |

USE EXAMPLES

In the use examples which follow, the compound from the prior art given below was employed as comparison compound (A).

Structure (A): A pyrrole ring with Cl at position 4, Cl at position 5, CN at position 3, N-CH$_2$-OC$_2$H$_5$ at position 1, and a 4-CF$_3$-phenyl group at position 2.

(disclosed in EP-A 0,347,488; see Example 9, page 27, line 42).

In the active compounds according to the invention, the numbers of the examples refer to the corresponding preparation examples.

Example A

Plutella test

Solvent: 7 parts by weight of dimethylformamide
Emulsifier: 1 part by weight of alkylaryl polyglycol ether To produce a suitable preparation of active compond, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) while the leaves are still moist.

After the specified periods of time, the destruction in % is determined. 100% means that all the caterpillars have been killed; 0% means that none of the caterpillars have been killed.

In this test, a superior activity compared with the prior art is shown, for example, by the following compounds of the preparation examples: (15), (19), (20), (21), (24), (25), (26), (27), (29), (30), (41).

After 7 days, the comparison compound (A) shows a degree of destruction of 20%, while each of the active compounds according to the invention shows a degree of destruction of 100%, in each case at an exemplary concentration of 0.001%.

Example B

Nephotettix test

Solvent: 7 parts by weight of dimethylformamide
Emulsifier: 1 part by weight of alkylaryl polyglycol ether To produce a suitable preparation of active compond, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of active compound of the desired concentration and are infested with larvae of the green rice cicada (*Nephotettix cincticeps*) while the seedlings are still moist.

After the specified periods of time, the destruction in % is determined. 100% means that all the cicadas have been killed; 0% means that none of the cicadas have been killed.

In this test, a superior activity compared with the prior art is shown, for example, by the following compounds of the preparation examples: (11).

After 7 days, the comparison compound (A) shows a degree of destruction of 20% and the active compound according to the invention a degree of destruction of 100%, in each case at an exemplary concentration of 0.01%.

Example C

Tetranychus test (OP resistant)

Solvent: 7 parts by weight of dimethylformamide
Emulsifier: 1 part by weight of alkylaryl polyglycol ether To produce a suitable preparation of active compond, 1 part by weight of active compound is mixed with the stated amount of solvent and the stated amount of emulsifier, and the concentrate is diluted with water to the desired concentration.

Bean plants (*Phaseolus vulgaris*) which are heavily infested with all development stages of the greenhouse red spider mite (*Tetranychus urticae*) are dipped into a preparation of active compound of the desired concentration.

After the specified periods of time, the effect in % is determined. 100% means that all spider mites have been killed; 0% means that none of the spider mites have been killed.

In this test, a superior activity compared with the prior art is shown, for example, by the following compounds of the preparation examples: (18), (19), (20), (24), (28), (30), (41).

At an exemplary concentration of 0.1% in each case, the active compounds according to the invention show degrees of destruction of 98 to 100% after 7 days while the comparison compound has no effect.

Example D

Fly test

Test animals: *Musca domestica*, strain WHO (N)
Solvent: 35 parts by weight of ethylene glycol monomethyl ether
Emulsifier: 35 parts by weight of monylphenol polyglycol ether To produce a suitable formulation, three parts by weight of active compound are mixed with seven parts of the abovementioned solvent/emulsifier mixture, and the resulting emulsion concentrate is diluted with water to the particular concentration desired.

2 ml of this preparation of active compound are pipetted onto filter paper discs ($\phi$9.5 cm) located in Petri dishes of suitable size. After the filter discs have dried, 25 test animals are transferred into the Petri dishes and covered.

After 6 hours, the effectiveness of the preparation of active compound is determined. The effectiveness is expressed as a percentage. 100% means that all flies have been killed; 0% means that none of the flies have been killed.

In this test, a superior activity compared with the prior art is shown, for example, by the following compounds of the preparation examples: ( 3 ), ( 19 ), ( 20 ), ( 26 ), ( 27 ), (28), (30), (41), (42).

At an exemplary concentration of 1000 ppm, the comparison compound (A) has no effect; in contrast, the effects of the abovementioned active compounds according to the invention are destruction rates of >50%, in some cases also 100%.

Example E

Blowfly larvae test

Test animals: *Lucilia cuprina* larvae
Solvent: 35 parts by weight of ethylene glycol monomethyl ether
Emulsifier: 35 parts by weight of nonylphenol polyglycol ether To produce a suitable preparation of active compound, three parts by weight of active compound are mixed with seven parts by weight of the abovementioned mixture and the emulsion concentrate thus obtained is diluted with water to the particular concentration desired.

About 20 Lucilia cuprina res. larvae are introduced into a test tube which contains approx. 1 cm³ of horse meat and 0.5 ml of the preparation of active compound. After 24 hours, the degree of destruction is determined. 100% means that all blowfly larvae have been killed; 0% means that none of the blowfly larvae have been killed.

In this test, a superior activity compared with the prior art is shown, for example, by the following compounds of the preparation examples: (9), (19), (20), (26), (27), (28), (30).

At an exemplary active compound concentration of 1000 ppm, the active compounds according to the invention in each case show a degree of destruction of 100%, while the comparison compound (A) has no effect.

Example F

Cockroach test

Test animals: *Blattella germanica* or *Periplaneta americana*
Solvent: 35 parts by weight of ethylene glycol monomethyl ether
Emulsifier: 35 parts by weight of nonylphenol polyglycol ether To produce a suitable formulation, three parts by weight of active compound are mixed with seven parts of the abovementioned solvent/emulsifier mixture, and the resulting emulsion concentrate is diluted with water to the particular concentration desired.

2 ml of this preparation of active compound are pipetted onto filter paper discs (φ9.5 cm) located in Petri dishes of a suitable size. After the filter discs have dried, 5 test animals in *B. germanica* or *P. americana* are transferred and covered.

After 3 days, the effectiveness of the preparation of active compound is determined. The effectiveness is expressed as a percentage. 100% means that all cockroaches have been killed; 0% means that none of the cockroaches have been killed.

In this test, a superior activity compared with the prior art is shown, for example, by the following compound of the preparation examples: (30).

At an exemplary concentration of 100 ppm, the active compound according to the invention results in a destruction rate of 100%, while the comparison compound (A) has an effectiveness of only approximately 50%, even when 1000 ppm are used.

It will be appreciated that the instant specification and claims are set forth by way of illustration and not imitation, and that various modifications and changes may be made without departing from the spirit and scope of the present invention.

We claim:

1. A substituted 2-arylpyrrole of the formula

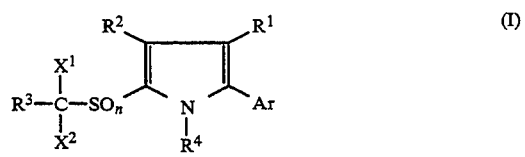

in which
$R^1$ and $R^2$ independently of one another represent hydrogen, bromine or chlorine, at least one of the radicals $R^1$ or $R^2$ representing bromine or chlorine,
$R^3$ represents hydrogen, halogen or $C_1$-$C_5$-alkyl (which is optionally substituted by identical or different substituents from the group consisting of 1 to 5 fluorine, chlorine or bromine atoms),
$R^4$ represents hydrogen or

in which $R^5$ represents hydrogen or $C_1$-$C_5$-alkyl (which is optionally substituted by 1 to 5 identical or different halogen atoms, by $C_1$-$C_5$-alkoxy, $C_1$-$C_5$-alkylthio, $C_1$-$C_5$-acyloxy, $C_2$-$C_6$-alkoxycarbonyl, phenyl, cyano or nitro) and
$R^6$ represents hydrogen or $C_1$-$C_6$-alkyl (which is optionally substituted by 1 to 5 identical or different halogen atoms, $C_1$-$C_8$-alkoxy, $C_1$-$C_8$-alkylthio, $C_1$-$C_6$-acyloxy, $C_2$-$C_8$-alkoxycarbonyl, phenyl, cyano or nitro) or in which $R^6$ represents

or —O—$R^7$ $R^7$ and $R^8$ independently of one another representing hydrogen, $C_1$-$C_8$-alkyl, $C_3$-$C_8$-alkenyl or $C_3$-$C_8$-alkinyl (the alkyl, alkenyl and alkinyl radicals in each case being optionally substituted by 1 to 6 identical or different halogen atoms, $C_1$-$C_6$-alkoxy, $C_1$-$C_6$-alkylthio, $C_1$-$C_6$-acyloxy, ($C_1$-$C_6$-alkoxy)-carbonyl, optionally substituted phenyl, cyano or nitro), or represent ($C_1$-$C_8$-alkoxy)-carbonyl, ($C_3$-$C_8$-alkenoxy)-carbonyl or ($C_3$-$C_8$-alkinoxy)-carbonyl, (the alkoxy, alkenoxy and alkinoxy radicals in each case being optionally substituted by 1 to 6 identical or different halogen atoms, $C_1$-$C_6$-alkoxy, $C_1$-$C_6$-alkylthio, $C_1$-$C_6$-acyloxy, ($C_1$-$C_8$-alkoxy)-carbonyl, optionally substituted phenyl, cyano, or nitro), or represent $C_1$-$C_8$-acyl (which is optionally substituted by 1 to 6 identical or different halogen atoms, $C_1$-$C_6$-alkoxy, $C_1$-$C_6$-alkylthio, $C_1$-$C_8$-acyloxy, ($C_1$-$C_8$-alkoxy)-carbonyl, optionally substituted phenyl, cyano or nitro), or in which $R^7$ and $R^8$ together with the N atom to which they are bonded form a 4- to 8-membered ring, Ar represents phenyl which is optionally monosubstituted to pentasubstituted by identical or different substituents wherein said substituents are halogen, optionally substituted $C_1$-$C_8$-alkyl, optionally substituted $C_2$-$C_8$-alkenyl, or optionally substituted $C_2$-$C_8$-alkinyl, wherein said substituents for the alkyl, alkenyl and alkinyl radicals are 1 to 6 halogen atoms, optionally substituted $C_1$-$C_5$-alkoxy, optionally substituted $C_1$-$C_5$-alkylthio or $C_1$-$C_5$-acyloxy, and said substituent for the alkoxy and alkylthio radicals are 1–6 halogen atoms, optionally substituted $C_1$-$C_8$-alkoxy, optionally substituted $C_2$-$C_8$-alkenoxy, or optionally substituted $C_2$-$C_8$-alkinoxy, wherein said substituents for the alkoxy, alkenoxy and alkinoxy radicals are 1 to 6 halogen atoms, optionally substituted $C_1$-$C_8$-alkylthio, optionally substituted $C_2$-$C_8$-alkenylthio, or optionally substituted $C_2$-$C_8$-alkinylthio wherein said substituents for the alkylthio, alkenylthio and alkinylthio radicals are 1 to 6 halogen atoms, $C_2$-$C_8$-acyloxy, which is optionally substituted by 1 to 6 halogen atoms, amino, which is optionally substituted by 1 to 2 identical or different $C_1$-$C_8$-alkyl radicals or $C_1$-$C_8$-halogenoalkyl radicals which contain 1 to 6 halogen atoms, nitro or cyano, and in which $X^1$ and $X^2$ independently of one another represent hydrogen, fluorine, chlorine or bromine and n represents 0, 1 or 2.

2. A substituted 2-arylpyrrole according to claim 1, in which $R^1$ and $R^2$ independently of one another represent hydrogen, bromine or chlorine, at least on of the two radicals $R^1$ or $R^2$ representing bromine or chlorine, $R^3$ represents hydrogen, fluorine, chlorine, bromine or $C_1$-$C_4$-alkyl (which is optionally substituted by identical or different substituents from the series consisting of 1 to 5 fluorine, chlorine or bromine atoms), $R^4$ represents hydrogen or

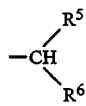

in which $R^5$ represents hydrogen or $C_1$-$C_4$-alkyl (which is optionally substituted by 1 to 5 identical or different halogen atoms, $C_1$-$C_4$-alkoxy, $C_1$-$C_4$-alkylthio, $C_1$-$C_4$-acyloxy, $C_2$-$C_5$-alkoxycarbonyl, phenyl, or cyano or nitro) and $R^6$ represents hydrogen or $C_1$-$C_5$-alkyl (which is optionally substituted by 1 to 5 identical or different halogen atoms, by $C_1$-$C_6$-alkoxy, $C_1$-$C_6$-alkylthio, $C_1$-$C_5$-acyloxy, $C_2$-$C_6$-alkoxycarbonyl, phenyl, ocyano or nitro), or in which $R^6$ represents

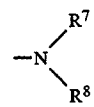

or —O—$R^7$ in which $R^7$ and $R^8$ independently of one another represent hydrogen, $C_1$-$C_6$-alkyl, $C_3$-$C_6$-alkenyl or $C_3$-$C_6$-alkinyl (the alkyl, alkenyl and alkinyl radicals in each case being optionally substituted by 1 to 5 fluorine and/or chlorine atoms, $C_1$-$C_4$-alkoxy, $C_1$-$C_4$-alkylthio, $C_1$-$C_4$-acyloxy, ($C_1$-$C_4$-alkoxy)-carbonyl, optionally substituted phenyl, cyano or nitro), or represent ($C_1$-$C_6$-alkoxy)-carbonyl, ($C_3$-$C_6$-alkenoxy)- or ($C_3$-$C_6$-alkinoxy)-carbonyl (the alkoxy, alkenoxy and alkinoxy radicals in each case optionally being substituted by 1 to 5 fluorine and/or chlorine atoms, $C_1$-$C_4$-alkoxy, $C_1$-$C_4$-alkylthio, $C_1$-$C_4$-acyloxy, ($C_1$-$C_4$-alkoxy)-carbonyl, optionally substituted phenyl, cyano or nitro), or represent $C_1$-$C_6$-acyl, which is optionally substituted by 1 to 5 fluorine and/or chlorine atoms, $C_1$-$C_4$-alkoxy, $C_1$-$C_4$-alkylthio, $C_1$-$C_4$-acyloxy, ($C_1$-$C_4$-alkoxy)-carbonyl, optionally substituted phenyl, cyano or nitro, or $R^7$ and $R^8$ together with the N atom to which they are bonded can be linked via any desired position to form a 4- to 6-membered ring;

in which furthermore

Ar represents phenyl which is optionally monosubstituted to tetrasubstituted by identical or different substituents wherein the substituents are fluorine, chlorine, or bromine, or optionally substituted $C_1$-$C_6$-alkyl, optionally substituted $C_2$-$C_6$-alkenyl, or optionally substituted $C_2$-$C_6$-alkinyl, wherein said substituent for the alkyl, alkenyl and alkinyl radicals are 1 to 5 fluorine, 1 to 5 chlorine atoms, $C_1$-$C_4$-alkoxy, $C_1$-$C_4$-alkylthio or by $C_1$-$C_4$-acyloxy, and said alkoxy and alkylthio radicals are optionally substituted by 1 to 5 fluorine and/or chlorine atoms, optionally substituted $C_1$-$C_6$-alkoxy, optionally substituted $C_2$-$C_6$-alkenoxy, or optionally substituted $C_2$-$C_6$-alkinoxy wherein said substituents for the alkoxy, alkenoxy and alkinoxy radicals are 1 to 5 fluorine atoms and 1 to 5 chlorine atoms, optionally substituted $C_1$-$C_6$-alkylthio, optionally substituted $C_2$-$C_6$-alkenylthio, or optionally substituted $C_2$-$C_6$-alkinylthio wherein said substituents for the alkylthio, alkenylthio and alkinylthio radicals are 1 to 5 fluorine and/or chlorine atoms, $C_2$-$C_6$-acyloxy, which is optionally substituted by 1 to 5 fluorine and/or chlorine atoms, amino, which is optionally substituted by 1 to 2 identical or different alkyl radicals which have 1 to 6 carbon atoms and are optionally substituted 1 to 5 fluorine and/or chlorine atoms, nitro or cyano, and in which $X^1$ and $X^2$ independently of one another represent hydrogen, fluorine or chlorine and n represents 0, 1 or 2.

3. An insecticidal, arachnicidal or nematocidal composition which comprises an insecticidally, arachnicidally or nematocidally effective amount of a compound according to claim 1 and a diluent.

4. A method of combatting insects, arachnids or nematodes which comprises applying to said insects, or arachnids or nematodes and/or their environment an insecticidally, arachnicidally or nematodically effective amount of a compound according to claim 1.

5. A substituted 2-arylpyrrole of the formula

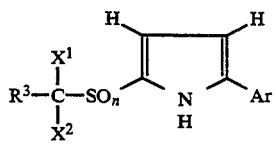 (II)

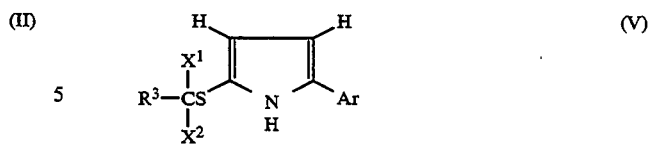 (V)

in which
n represents 1 or 2,
Ar represents phenyl which is optionally monosubstituted to pentasubstituted by identical or different substituents wherein said substituents are halogen,
optionally substituted $C_1$–$C_8$-alkyl, optionally substituted $C_2$–$C_8$-alkenyl, or optionally substituted $C_2$–$C_8$-alkinyl, wherein said substituents for the alkyl, alkenyl and alkinyl radicals are 1 to 6 halogen atoms, optionally substituted $C_1$–$C_5$-alkoxy, optionally substituted $C_1$–$C_5$-alkylthio or $C_1$–$C_5$-acyloxy, and said substituent for the alkoxy and alkylthio radicals are 1–6 halogen atoms,
optionally substituted $C_1$–$C_8$-alkoxy, optionally substituted $C_2$–$C_8$-alkenoxy, or optionally substituted $C_2$–$C_8$-alkinoxy, wherein said substituents for the alkoxy, alkenoxy and alkinoxy radicals are 1 to 6 halogen atoms,
optionally substituted $C_1$–$C_8$-alkylthio, optionally substituted $C_2$–$C_8$-alkenylthio, or optionally substituted $C_2$–$C_8$-alkinylthio and alkinylthio radicals are 1 to 6 halogen atoms,
$C_2$–$C_8$-acyloxy, which is optionally substituted by 1 to 6 halogen atoms,
amino, which is optionally substituted by 1 to 2 identical or different $C_1$–$C_8$-alkyl radicals or $C_1$–$C_8$-halogenoalkyl radicals which contain 1 to 6 halogen atoms,
nitro or cyano,
$R^3$ represents hydrogen, halogen or $C_1$–$C_5$-alkyl (which is optionally substituted by identical or different substituents from the group consisting of 1 to 5 fluorine, chlorine or bromine atoms and
$X^1$ and $X^2$ independently of one another represent hydrogen or halogen.

6. A substituted 2-arylpyrrole of the formula in which
Ar represents phenyl which is optionally monosubstituted to pentasubstituted by identical or different substituents wherein said substituents are halogen,
optionally substituted $C_1$–$C_8$-alkyl, optionally substituted $C_2$–$C_8$-alkenyl, or optionally substituted $C_2$–$C_8$-alkinyl, wherein said substituents for the alkyl, alkenyl and alkinyl radicals are 1 to 6 halogen atoms, optionally substituted $C_1$–$C_5$-alkoxy, optionally substituted $C_1$–$C_5$-alkylthio or $C_1$–$C_5$-acyloxy, and said substituent for the alkoxy and alkylthio radicals are 1–6 halogen atoms,
optionally substituted $C_1$–$C_8$-alkoxy, optionally substituted $C_2$–$C_8$-alkenoxy, or optionally substituted $C_2$–$C_8$-alkinoxy, wherein said substituents for the alkoxy, alkenoxy and alkinoxy radicals are 1 to 6 halogen atoms,
optionally substituted $C_1$–$C_8$-alkylthio, optionally substituted $C_2$–$C_8$-alkenylthio, or optionally substituted $C_2$–$C_8$-alkinylthio wherein said substituents for the alkylthio, alkenylthio and alkinylthio radicals are 1 to 6 halogen atoms,
$C_2$–$C_8$-acyloxy, which is optionally substituted by 1 to 6 halogen atoms,
amino, which is optionally substituted by 1 to 2 identical or different $C_1$–$C_8$-alkyl radicals or $C_1$–$C_8$-halogenoalkyl radicals which contain 1 to 6 halogen atoms,
nitro or cyano,
$R^3$ represents hydrogen, halogen or $C_1$–$C_5$-alkyl (which is optionally substituted by identical or different substituents from the group consisting of 1 to 5 fluorine, chlorine or bromine atoms and
$X^1$ and $X^2$ independently of one another represent hydrogen or halogen.

* * * * *